(12) United States Patent
Robertson et al.

(10) Patent No.: US 7,288,400 B2
(45) Date of Patent: Oct. 30, 2007

(54) NUCLEIC ACIDS ENCODING ESTERASES AND METHODS OF MAKING AND USING THEM

(75) Inventors: Dan E. Robertson, San Diego, CA (US); Dennis Murphy, Malvern, PA (US); John Reid, Ardmore, PA (US); Anthony M. Maffia, Old Bridge, NJ (US); Steven Link, Wilmington, DE (US); Ronald V. Swanson, Del Mar, CA (US); Patrick V. Warren, Coatesville, PA (US); Anna Kosmotka, Perkiomenville, PA (US); Jay M. Short, Rancho Santa Fe, CA (US); Eric J. Mathur, Carlsbad, CA (US)

(73) Assignee: Verenium Corporation, San Diego, CA (US)

( * ) Notice: Subject to any disclaimer, the term of this patent is extended or adjusted under 35 U.S.C. 154(b) by 0 days.

(21) Appl. No.: 09/903,410

(22) Filed: Jul. 10, 2001

(65) Prior Publication Data

US 2002/0146799 A1    Oct. 10, 2002

Related U.S. Application Data

(63) Continuation-in-part of application No. 09/382,242, filed on Aug. 24, 1999, now abandoned, which is a continuation of application No. 08/602,359, filed on Feb. 16, 1996, now Pat. No. 5,942,430.

(51) Int. Cl.
*C12N 15/55* (2006.01)
*C12N 9/15* (2006.01)

(52) U.S. Cl. .................... 435/197; 435/198; 435/252.3; 435/325; 435/419; 435/348; 435/254.11; 435/254.2; 435/320.1; 536/23.2

(58) Field of Classification Search ............... 536/23.2, 536/23.1; 435/196, 197, 198, 252.3, 325, 435/419, 348, 254.11, 254.2, 320.1
See application file for complete search history.

(56) References Cited

U.S. PATENT DOCUMENTS 5,306,636 A    4/1994    Iizumi et al. ............ 435/252.3

FOREIGN PATENT DOCUMENTS

| EP | 0 318 775 A | | 6/1989 |
|---|---|---|---|
| WO | 93 25691 A | | 12/1993 |
| WO | 94 02617 A | | 2/1994 |
| WO | 95 23853 | | 9/1995 |
| WO | 95 34644 A | | 12/1995 |
| WO | 97/30160 | * | 8/1997 |

OTHER PUBLICATIONS

Wong et al. GenBank Accession No. S72930. (May 1993).*
Taylor et al. GenBank Accession No. X00520. (Jun. 1983).*
P. Bork, Genome Research, 10:398-400. (2000).*
F.J. Van de Loo et al., Proc. Natl. Acad. Sci. 92(15): 6743-6747. (Jul. 1995).*
P. Broun et al., Science 282:1315-1317. ( Nov. 1998).*
J. Seffernick et al. Journal of Bacteriology, vol. 183(8): 2405-2410. (Apr. 2001).*
A. Witkowski et al., Biochemistry 38:1 1643-11650. (1999).*
H. Guo et al., "Protein Tolerance to Random Amino Acid Change", PNAS 101(25): 9205-9210. (Jun. 2004).*
Kugimiya Wataru et al., "Molecular cloning and structure of the gene for esterase from a thermophilic bacterium, Bacillus stearothermophilus IFO 12550," *Bioscience Biotechnology and Biochemistry* 56(12):2074-2075 (1992) XP002138593.
Huddleston S., et al., "The identification and partial characterisation of a novel inducible extracellular thermostable esterase from the archaeon Sulfolobus shibatae," *Biochemical and Biophysical Research Communications* 216(2):495-500 (1995) XP002138594.
Wray L., et al., "Streptomyces coelicolor transcription factor, AC L03213," *EBI Database* Oct. 9, 1992 XP002145895.
Canganella, et al., "Characterization of amylolytic and pullulytic enzymes from thermophilic archaea and from a new *Fervidobacterium* species" *App. Microbiol. Biotechnol.* 42:239-245 (1994).
Cornec, et al, Derwent Biotechnology Abstracts, 13(15):95-96 (1994) Abstract No. 94-08869, "Thermostable Esterase Activity from Deep-Sea Sulfur Dependent Thermophilic Archaebacteria—Thermostable Enzyme Purification From Thermophilic Archaebacterium and Characterization" *Themophiles Sci Technol.* 18 (1992).
Kim, et al., "Structure and Organization of the Human Transglutaminase 1 Gene" *The Journal of Biological Chemistry* 267(11):7710-7717 (1992).
Ladrat, et al, Derwent Biotechnology Abstracts, 14 (15):p125 (1995) Abstract No. 95-09223, Thermostable Enzymes Screened on Thermophilic Microorganisms from Deep-Sea Hydrothermal Vents—βGlucosidase, Alcohol Dehydrogenase, Protease and Esterase Activity *C.R. Seances Acad. Sci.*, Ser 3., 318(4):423-429 (1995).
GenBank entry X86487 (Jan. 1996).
European Search Report for EP 04 01 7203, mailed on Mar. 15, 2007, 8 pages.
EBI Database Accession No. P36165, Jun. 1, 1994, Garcia-Cantalejo et al.
Garcia-Cantalejo et al., Yeast (1994) 10:231-245.

* cited by examiner

*Primary Examiner*—Rebecca Prouty
(74) *Attorney, Agent, or Firm*—Morrison & Foerster LLP

(57) ABSTRACT

The invention relates to esterases and to polynucleotides encoding the esterases. In addition methods of designing new esterase method of use thereof are also provided. The esterases have increased activity and stability at increased pH and temperature.

23 Claims, 21 Drawing Sheets

FIG. 5
Staphylothermus Marinus - F1-12LC

```
  1 ATG TCT TTA AAC AAG CAC TCT TGG ATG GAT ATG ATA ATA TTT ATT CTC AGC TTT TCT TTC   60
  1 Met Ser Leu Asn Lys His Ser Trp Met Asp Met Ile Ile Phe Ile Leu Ser Phe Ser Phe   20

61 CCA TTA ACA ATG ATC GCA TTA GCT GCA TCT TCT ATG TCG TCA TGG TTT AAT ATA TGG AAT  120
 21 Pro Leu Thr Met Ile Ala Leu Ala Ala Ser Ser Met Ser Ser Trp Phe Asn Ile Trp Asn   40

121 GCA TTA AGC GAT CTA GGA CAT GCT GTT AAA AGC AGT GTT GCT CCA ATA TTC AAT CTA GGT  180
 41 Ala Leu Ser Asp Leu Gly His Ala Val Lys Ser Ser Val Ala Pro Ile Phe Asn Leu Gly   60

181 CCT GCA ATT GGT GGG ATA CTA ATT GGT TTA ATA GTT GGT TTA AGA AAT CTT TAT TCG TGG AGT  240
 61 Leu Ala Ile Gly Gly Ile Leu Ile Gly Leu Ile Val Gly Leu Arg Asn Leu Tyr Ser Trp Ser   80

241 AGA GTT AAA GGA TCT TTA ATC ATA TCC ATG GGT GTA TTT CTT AAC TTA ATA GGG GTT TTC  300
 81 Arg Val Lys Gly Ser Leu Ile Ile Ser Met Gly Val Phe Leu Asn Leu Ile Gly Val Phe  100

301 GAC GAA GTA TAT GGT TGG ATA CAT TTC CTA GTC TCA TTG TTT CTC GTA TGG ATA CTA ATA  360
101 Asp Glu Val Tyr Gly Trp Ile His Phe Leu Val Ser Leu Phe Leu Val Trp Ile Leu Ile  120

361 GCA TTC ATA GCT ATA TCA CTT GAC AAA TCA CTT GCT TCA TGG ATA GCT GTT CTA CTA ATA  420
121 Ala Phe Ile Ala Ile Ser Leu Asp Lys Ser Leu Ala Ser Trp Ile Ala Val Leu Leu Ile  140

421 GGT CAT ATT GCA ATG TGG TAT CTA CAC TTT GCT TCA GAG ATT CCG AGA GGT GCG GCT ATT  480
141 Gly His Ile Ala Met Trp Tyr Leu His Phe Ala Ser Glu Ile Pro Arg Gly Ala Ala Ile  160

481 CCC GAG TTA TTA GCG GTA TTC TCG TTT TTA CCA TTC TAT ATA AGA GAC TAT TTT AAA TCA  540
161 Pro Glu Leu Leu Ala Val Phe Ser Phe Leu Pro Phe Tyr Ile Arg Asp Tyr Phe Lys Ser  180

541 TAC ACT AAA CGA TAG                                                               555
181 Tyr Thr Lys Arg End                                                               185
```

FIG. 6A
Pyrodictium - TAG11-17LC

```
  1 ATG AAA CTC CTT GAG CCC ACA AAT ACC TCC TAC ACG CTG TTA CAG GAT TTA GCA TTG CAT   60
  1 Met Lys Leu Leu Glu Pro Thr Asn Thr Ser Tyr Thr Leu Leu Gln Asp Leu Ala Leu His   20

61 TTT GCA TTT TAC TGG TTT CTG GCC GTG TAT GTG GCC TGG TTA ACG TGG TTA CCC GGT GTC CTA GTC CGG GGC  120
 21 Phe Ala Phe Tyr Trp Phe Leu Ala Val Tyr Val Ala Trp Leu Thr Trp Leu Pro Gly Val Leu Val Arg Gly   40

121 GTA GCT GTG GAC ACA GGG GCT GTC TTG GCT CGG GCT CGG GTT CCT CGG GTG CCT GGG GTG AAG AGG CTG  180
 41 Val Ala Val Asp Thr Gly Ala Val Leu Ala Arg Val Ala Arg Gly Leu Gly Arg Arg Gly Lys Arg Leu   60

181 CTC CTG GCC GCT GTG GCT GTT GTG TCC GTT GTG CCG GCT TAT GTG  240
 61 Leu Leu Ala Ala Val Ala Val Val Ser Val Val Pro Ala Tyr Val   80

241 GCG TAT AGT AGT CTG CAC CCG GAG AGC TGT CGG CCC GTT GCG CCG CTC ACC TAC  300
 81 Ala Tyr Ser Ser Leu His Pro Glu Ser Cys Arg Pro Val Ala Pro Glu Gly Leu Thr Tyr  100

301 AAA GAG TTC AGC GTG ACC GCG GAG GAT GGC TTG GTG GTT CGG GGC TGG GTG GTG CTG GGC CCC  360
101 Lys Glu Phe Ser Val Thr Ala Glu Asp Gly Leu Val Val Arg Gly Trp Val Leu Gly Pro  120

361 GGC GCT GGG GGC AAC CCG GTT TTG ATG CAC GGG TAT ACT GGG TGC CGC TCG GCG  420
121 Gly Ala Gly Gly Asn Pro Val Phe Leu Met His Gly Tyr Thr Gly Cys Arg Ser Ala  140

421 CCC TAC ATG GCT GTG CTG GCC CTC GTG GAG CTC GTG GAG TGG GGC TAC CCG GTT GTT TTC  480
141 Pro Tyr Met Ala Val Leu Ala Leu Val Glu Leu Val Glu Trp Gly Tyr Pro Val Val Phe  160

481 GAC TTC CGG GGC CAC GGG GAG AGC GGG GGG TCG ACG ATT GGG CCC CGG GTG GAG GTG CTG  540
161 Asp Phe Arg Gly His Gly Glu Ser Gly Gly Ser Thr Ile Gly Pro Arg Val Glu Val Leu  180

541 GAT GCC CGG GCT GTG GGC TAT GTC TCG GAG CGG TTC CCC GGC CGC CGG ATA ATA TTG  600
181 Asp Ala Arg Ala Val Gly Tyr Val Ser Glu Arg Phe Pro Gly Arg Arg Ile Ile Leu  200
```

FIG. 4B
Pyrodictium - TAG11-17LC

```
601 GTG GGG TTC AGT ATG GGC GGC GCT GTA GCG ATC GTG GAG GGT GCT GGG GAC CCG CGG GTC   660
201 Val Gly Phe Ser Met Gly Gly Ala Val Ala Ile Val Glu Gly Ala Gly Asp Pro Arg Val   220

661 TAC GCG GTG GCT GCT GAT AGC CCG CTG TAT AGG CTC CGG GAC GTC ATA CCC CGG TGG CTG   720
221 Tyr Ala Val Ala Ala Asp Ser Pro Leu Tyr Arg Leu Arg Asp Val Ile Pro Arg Trp Leu   240

721 GAG TAC AAG ACG CCG CTG CCG GGC TGG GTG CTG GTG GTG CTG GCC GGG TTC TAC GGG AGG CTG   780
241 Glu Tyr Lys Thr Pro Leu Pro Gly Trp Val Leu Val Gly Val Leu Ala Gly Phe Tyr Gly Arg Leu   260

781 ATG GGC GGC GTT GAC CTC GGC TTC GGC CCC GCT GGG GTG GAG CGC GTG GAT AAG CCG TTG   840
261 Met Ala Gly Val Asp Leu Gly Phe Gly Pro Ala Gly Val Glu Arg Val Asp Lys Pro Leu   280

841 CTG GTG TAT GGG CCC CGG GAC CCG CTG GTG ACG CGG CTG ACG CGC AGG AGC CTG GCG   900
281 Leu Val Tyr Gly Pro Arg Asp Pro Leu Val Thr Arg Asp Arg Ser Leu Ala   300

901 TCC AGC CGT AGC CCG TGT CTC GAG GTT CTC GTC GAG CTC CCT GGG GCT GGC GTG GAG GCC GTG   960
301 Ser Arg Ser Pro Cys Leu Glu Val Leu Val Glu Leu Pro Gly Ala Gly His Val Glu Ala Val   320

961 GAT GTG CTC GGG CGG CTG GGC TAC GCA GAC ATG CTG ATA GAG CTG GCG CAC GAG GAG TGC   1020
321 Asp Val Leu Gly Arg Leu Gly Tyr Ala Asp Met Leu Ile Glu Leu Ala His Glu Glu Cys   340

1021 CCT CCG GGG GCC GGT GGC TGA   1041
341 Pro Pro Gly Ala Gly Gly End   347
```

FIG. 7A
Archaeoglobus Veniificus SN P6-24LC

```
  1 ATG CCA TAT GTT AGG AAT GGT GTA AAT ATC TAT GAA CTG GTG GAT GGA CCT GAG   60
  1 Met Pro Tyr Val Arg Asn Gly Val Asn Ile Tyr Glu Leu Val Asp Gly Pro Glu   20

61 CCA CCA ATT GTC TTT GTT CAC GGA ACA GCA AAT ATG TGG AAA GAG CAA AGA      120
 21 Pro Pro Ile Val Phe Val His Gly Thr Ala Asn Met Trp Lys Glu Gln Arg       40

121 CGT TAT TTT GCA GGC AGG AAT ATG ATG TTG TTT GAT AAC AGA GGT CAG GGC AGG TCC  180
 41 Arg Tyr Phe Ala Gly Arg Asn Met Met Leu Phe Asp Asn Arg Gly His Gly Arg Ser  60

181 GAT AAG CCA CTT GGA TAC GAT TTC TAC AGA TTT GAG AAC TTC ATT TCA GAT TTA GAT GCG  240
 61 Asp Lys Pro Leu Gly Tyr Asp Phe Tyr Arg Phe Glu Asn Phe Ile Ser Asp Leu Asp Ala  80

241 GTT GTT AGG GAG ACT GGA GTG AAA TTT GTT CTC GTC GGA CAT TCA TTC GGA ACA ATG  300
 81 Val Val Arg Glu Thr Gly Val Lys Phe Val Leu Val Gly His Ser Phe Gly Thr Met  100

301 ATC TCT ATG AAG TAC TGT TCG GAG AAT CGG TAT CTT GCT CTA ATC CTC ATA GGT      360
101 Ile Ser Met Lys Tyr Cys Ser Glu Asn Arg Tyr Leu Ala Leu Ile Leu Ile Gly      120

361 GGT GGG AGC AGA ATA AAG CTT CTA CAC AGA ATT GGA TAT CCT TTA GCA AAG ATT CTT GCA  420
121 Gly Gly Ser Arg Ile Lys Leu Leu His Arg Ile Gly Tyr Pro Leu Ala Lys Ile Leu Ala  140

421 TCC ATT GCA TAC AAG AAG TCT TCA AGA TTG GTC GCA GAT CTT TCC TTT GGC AAA AAT GCT  480
141 Ser Ile Ala Tyr Lys Lys Ser Ser Arg Leu Val Ala Asp Leu Ser Phe Gly Lys Asn Ala  160

481 GGT GAA CTT AAA GAG TGG GGA TGG AAA CAG GCA ATG GAT TAT ACA CCC TCC TAC GTG GCA  540
161 Gly Glu Leu Lys Glu Trp Gly Trp Lys Gln Ala Met Asp Tyr Thr Pro Ser Tyr Val Ala  180

541 ATG TAC ACG TAC ACT CTA ACG AAA GTT GAA AAT CTT GAG AAT ATC TTG GAG AAA ATA GAC  600
181 Met Tyr Thr Tyr Thr Leu Thr Lys Val Glu Asn Leu Glu Asn Ile Leu Glu Lys Ile Asp  200

601 TGT CCA ACA CTG ATC GTT GGA GAT GCA CTA TTG CCC GTT AGC AAA TCA GTT         660
201 Cys Pro Thr Leu Ile Val Gly Asp Ala Leu Leu Pro Val Ser Lys Ser Val         220
```

FIG. 7B
Archaeoglobus Venificus SN P6-24LC

```
661 GAG CTG ACG AGG AGG ATA GAA AAC TCA AAG CTT GTG ATC ATC CCA AAC TCG GGG CAT TGC 720
221 Glu Leu Thr Arg Arg Ile Glu Asn Ser Lys Leu Val Ile Ile Pro Asn Ser Gly His Cys 240

721 GTA ATG CTT GAG AGT CCA AGT GAG GTT AAT AGA GCA ATG GAC GAA TTC ATT TCT TCA GCA 780
241 Val Met Leu Glu Ser Pro Ser Glu Val Asn Arg Ala Met Asp Glu Phe Ile Ser Ser Ala 260

781 CAG TTC TAA                                                                    789
261 Gln Phe End                                                                   263
```

FIG. 8
Aquifax pyrophilus - 28LC

```
  1 TTG AGA TTG AGG AAA TTT GAA GAG ATA AAC CTC GTT CTT TCG GGA GGA GCT GCA AAG GGC   60
  1 Leu Arg Leu Arg Lys Phe Glu Glu Ile Asn Leu Val Leu Ser Gly Gly Ala Ala Lys Gly   20

61 ATA GCC CAC ATA GGT GTT TTG AAA GCT ATA AAC GAG CTC GGT ATA GGT GTG AGG GCT TTA  120
 21 Ile Ala His Ile Gly Val Leu Lys Ala Ile Asn Glu Leu Gly Ile Gly Val Arg Ala Leu   40

121 AGC GGG GTG AGC GCC GGG GCA ATC GTT TCG GTC TTT TAT GCC TCA GGC TAC TCC CCT GAA  180
 41 Ser Gly Val Ser Ala Gly Ala Ile Val Ser Val Phe Tyr Ala Ser Gly Tyr Ser Pro Glu   60

181 GGG ATG TTC AGC CTT CTG AAG GTA AAC TGG CTG AAG CTG TTT AAG TTC AAG CCA CCT      240
 61 Gly Met Phe Ser Leu Leu Lys Val Asn Trp Leu Lys Leu Phe Lys Phe Lys Pro Pro      80

241 CTG AAG GGA TTG ATA GGG GAG AAG GCT ATA AGA TTC CTT GAG GAA GTT CTC CCT TAC      300
 81 Leu Lys Gly Leu Ile Gly Glu Lys Ala Ile Arg Phe Leu Glu Glu Val Leu Pro Tyr     100

301 AGG AGA ATA GAA AAA CTT GAG GAA TAC CCG ACG TAT ATA TGC GCG ACG TTA TAC TCG GGA  360
101 Arg Arg Ile Glu Lys Leu Glu Glu Tyr Pro Thr Tyr Ile Cys Ala Thr Leu Tyr Ser Gly  120

361 AGG GCT CTA TAC CTC TCG GAG AGT TTA ATC CCC GCA CTT GTC TGC AGC TGT GCA ATT      420
121 Arg Ala Leu Tyr Leu Ser Glu Ser Leu Ile Pro Ala Leu Val Cys Ser Cys Ala Ile     140

421 CCC GGC ATA TTT GAA CTT TTC GAA TAT GGT TAT CTT GTT GAC GGA GGT ATA GTT         480
141 Pro Gly Ile Phe Glu Leu Phe Glu Tyr Gly Tyr Leu Val Asp Gly Gly Ile Val         160

481 AAC AAC CTT CCC GTT GAG CCC TTT CAG GAA AGC GGT ATT CTT ACC GTT TGC GTT GAT GTC  540
161 Asn Asn Leu Pro Val Glu Pro Phe Gln Glu Ser Gly Ile Leu Thr Val Cys Val Asp Val  180

541 CTT CCC ATA GAG CCG GAA AAG GAT ATA AAG AAC ATT CTT CAC ATC TTG CTT TTG AGC TTC  600
181 Leu Pro Ile Glu Pro Glu Lys Asp Ile Lys Asn Ile Leu His Ile Leu Leu Leu Ser Phe  200

601 TTT CTT GCG GTC CGC TCA AAC TCC AAC AGA AAG GAG TTT TGT GAC TTC GTT ATA GTT      660
201 Phe Leu Ala Val Arg Ser Asn Ser Asn Arg Lys Glu Phe Cys Asp Phe Val Ile Val     220

661 CCT GAG CTT GAG GAG TTC ACA CCC CTT GAT GTT AGA GCG AAA CAA ATA ATG GAG AGG      720
221 Pro Glu Leu Glu Glu Phe Thr Pro Leu Asp Val Arg Ala Lys Gln Ile Met Glu Arg     240

721 GGA TAC ATA AAG GCC TTA GAG GTA CTT TCT GAA TAG                                  756
241 Gly Tyr Ile Lys Ala Leu Glu Val Leu Ser Glu End                                  252
```

FIG. 9A
M11TL-29L

```
  1 ATG TTT AAT ATC AAT GTC TTT GTT AAT ATA TCT TGG CTG TAT TTT TCA GGG ATA GTT ATG   60
  1 Met Phe Asn Ile Asn Val Phe Val Asn Ile Ser Trp Leu Tyr Phe Ser Gly Ile Val Met   20

61 AAG ACT GTG GAA GAG TAT GCG CTA CTT GAA ACA GGC GTA AGA GGC TTT TAT CGG TGT GTA  120
 21 Lys Thr Val Glu Glu Tyr Ala Leu Leu Glu Thr Gly Val Arg Gly Phe Tyr Arg Cys Val   40

121 ATC CCG GAG AAA GCT TTT AAC ACT TTG ATA ATA GGT TCA CAC GGA TTG GGG GCG CAC AGT  180
 41 Ile Pro Glu Lys Ala Phe Asn Thr Leu Ile Ile Gly Ser His Gly Leu Gly Ala His Ser   60

181 GGA ATC TAC ATT AGT GTT GCT GAA TTT GCT AGG CAC GGA TTC TGC ATG CAC  240
 61 Gly Ile Tyr Ile Ser Val Ala Glu Phe Ala Arg His Gly Phe Cys Met His   80

241 GAT CAA AGG GGA CAT GGG AGA ACG GAT AGA AGA GAA GAG CTT TAT GTG GAG GGC TTT  300
 81 Asp Gln Arg Gly His Gly Arg Thr Asp Arg Arg Glu Glu Leu Tyr Val Glu Gly Phe  100

301 CAC AAC TTC ATA GAG GAT ATG AAG GCC TTC TCC GAT TAT TGG CGC GTG GGA GGT  360
101 His Asn Phe Ile Glu Asp Met Lys Ala Phe Ser Asp Tyr Trp Arg Val Gly Gly  120

361 GAC GAA ATA ATA TTG GGA CTA AGT ATG GGC GGG GTG CTG ATA GCG CTC TTA ACA GTT GCA  420
121 Asp Glu Ile Ile Leu Gly Leu Ser Met Gly Gly Val Leu Ile Ala Leu Leu Thr Val Ala  140

421 ACT TAT AAA GAA ATC GCC AAG GGA GTT ATC GCG CTA GCC CCG GCC CTC CAA ATC CCC TTA  480
141 Thr Tyr Lys Glu Ile Ala Lys Gly Val Ile Ala Leu Ala Pro Ala Leu Gln Ile Pro Leu  160

481 ACC CCG GCT AGA AGA CTT GTT CTA AGC CTC GCG TCA GAG CTT GCC CAT TCT AAG ATC  540
161 Thr Pro Ala Arg Arg Leu Val Leu Ser Leu Ala Ser Arg Leu Ala Pro His Ser Lys Ile  180

541 ACC TTA CAA AGG AGA TTG CCG CAG AAA CCA GAG GGT TTT CAA GCA AAA GAT ATA GAA  600
181 Thr Leu Gln Arg Arg Leu Pro Gln Lys Pro Glu Gly Phe Gln Ala Lys Asp Ile Glu  200

601 TAC AGT CTG AGT GAA ATA TCA GTC AAG CTC GTG GAC AAT ATG GAA CTG CTT ATT CAT GGG AAA TCA TCT ATG  660
201 Tyr Ser Leu Ser Glu Ile Ser Val Lys Leu Val Asp Asn Met Glu Leu Leu Ile His Gly Lys Ser Ser Met  220

661 TTG TGG ACC ATA GGG GAA ATT AAT ACT CCC GTC CTG CTT ATT CAT GGG AAA TCA TCT ATG  720
221 Phe Trp Thr Ile Gly Glu Ile Asn Thr Pro Val Leu Leu Ile His Gly Lys Ser Ser Met  240
```

FIG. 9B
M11TL-29L

```
721 AAT GTC ATA CCT CCG GAG GCG AGC AAA AAA GCC TAC CAA TTA ATA CCT TCA TTC CCT AAA 780
241 Asn Val Ile Pro Pro Glu Ala Ser Lys Lys Ala Tyr Gln Leu Ile Pro Ser Phe Pro Lys 260

781 GAG TTG AAA ATA TAC CCC GAT CTT GGA CAC AAC TTG TTT GAA CCA GGC GTG AAA 840
261 Glu Leu Lys Ile Tyr Pro Asp Leu Gly His Asn Leu Phe Glu Pro Gly Val Lys 280

841 ATC GTC ACA GAC ATT GTA GAG TGG GTT AAG AAT CTA CCC AGG GAA AAT CCT TAA 894
281 Ile Val Thr Asp Ile Val Glu Trp Val Lys Asn Leu Pro Arg Glu Asn Pro End 298
```

FIG. 10A
Thermococcus CL-2-30LC

```
  1 ATG GAG GTT TAC AAG GCC AAA TTC GGC GAA GCA AAG CTC GGC TGG GTC GTT CTG GTT CAT   60
  1 Met Glu Val Tyr Lys Ala Lys Phe Gly Glu Ala Lys Leu Gly Trp Val Val Leu Val His   20

61 GGC CTC GGC GAG CAC AGC AGG TAT GGA AGA CTG ATT AAG GAA CTC AAG GAA CTC AAC TAT GCC GGC  120
 21 Gly Leu Gly Glu His Ser Arg Tyr Gly Arg Leu Ile Lys Glu Leu Asn Tyr Ala Gly   40

121 TTT GGA GTT TAC ACC TTC GAC TGG CCC GGC CAC GGG AAG AGC CCG GGG AAG AGA GGG CAC  180
 41 Phe Gly Val Tyr Thr Phe Asp Trp Pro Gly His Gly Lys Ser Pro Gly Lys Arg Gly His   60

181 ACG AGC GTC GAG GAG ATG GAA ATC GAC TCG ATA ATC GAG GAG ATC AGG GAG AAG  240
 61 Thr Ser Val Glu Glu Met Glu Ile Asp Ser Ile Ile Glu Glu Ile Arg Glu Lys   80

241 CCC TTC CTC TTC GGC CAC AGC CTC GGT CTA ACT GTC ATC AGG TAC GCT GAG ACG CGG  300
 81 Pro Phe Leu Phe Gly His Ser Leu Gly Leu Thr Val Ile Arg Tyr Ala Glu Thr Arg  100

301 CCC GAT AAA ATA CGG GGA TTA ATA GCT TCC TCG CCT GCC CTC GCC AAG AGC CCG GAA ACG  360
101 Pro Asp Lys Ile Arg Gly Leu Ile Ala Ser Ser Pro Ala Leu Ala Lys Ser Pro Glu Thr  120

361 CCG GGC TTC ATG GTG GCC AAG TTC CTT GGA AAG ATC GCC CCG GGA GTT GTT CTC  420
121 Pro Gly Phe Met Val Ala Lys Phe Leu Gly Lys Ile Ala Pro Gly Val Val Leu  140

421 TCC AAC GGC ATA AAG CCG GAA CTC CTC TCG AGG AAC AGG GAC GCC GTG AGG TAC GTT  480
141 Ser Asn Gly Ile Lys Pro Glu Leu Leu Ser Arg Asn Arg Asp Ala Val Arg Tyr Val  160

481 GAA GAC CCA CTC GTC CAC GAC AGG ATT TCG GCC AAG CTG GGA AGG AGC ATC TTC GTG AAC  540
161 Glu Asp Pro Leu Val His Asp Arg Ile Ser Ala Lys Leu Gly Arg Ser Ile Phe Val Asn  180

541 ATG GAG GCC GCC CAC GAG GCG CAC AGG GAA GAA ATA AAA GTC CTC GTC CTT CTG ATG GGC  600
181 Met Glu Ala Ala His Glu Ala His Arg Glu Glu Ile Lys Val Leu Val Pro Ile Leu Leu Met Gly  200

601 ACT GGC GAT GTA ATA ACC GAA CCT TCA CGC AGA CGC TTC GAG GAG CTG GCC GTC  660
201 Thr Gly Asp Val Ile Thr Pro Gly Ser Arg Arg Leu Phe Glu Glu Leu Ala Val  220

661 GAG AAC AAA ACC CTG AGG GAG TTC CAC GGG TAC CGC AGA TAT TT GAA GAC CCC GAG  720
221 Glu Asn Lys Thr Leu Arg Glu Phe His Gly Tyr Ala Tyr His Glu Ile Phe Glu Asp Pro Glu  240
```

FIG.10B
Thermococcus CL-2-30LC

```
721 TGG GCC GAG GAG TTC CAC GAA ACA ATT GTT AAG TGG CTG GTT GAA AAA TCG TAC TCT TCG  780
241 Trp Ala Glu Glu Phe His Glu Thr Ile Val Lys Trp Leu Val Glu Lys Ser Tyr Ser Ser  260

781 GCT CAA TAA  789
261 Ala Gln End  263
```

FIG. 11
Aquifex VF5-34LC

```
  1 TTG ATT GGC AAT TTG AAA TTG AAG AGG TTT GAA GAG GTT AAC TTA GTT CTT TCG GGA GGG   60
  1 Leu Ile Gly Asn Leu Lys Leu Lys Arg Phe Glu Glu Val Asn Leu Val Leu Ser Gly Gly   20

61 GCT GCC AAG GGT ATC GCC CAT ATA GGT TTA AAA GCT GTT CTG GAA GCT CTG GGT CTC AAG  120
 21 Ala Ala Lys Gly Ile Ala His Ile Gly Leu Lys Ala Val Leu Glu Ala Leu Gly Leu Lys   40

121 GTA AAG AGG CTC AGC GGG GTA AGT GCT GGA GCT ATC GTT TCC GTT TTT TAC GCT TCG GGC  180
 41 Val Lys Arg Leu Ser Gly Val Ser Ala Gly Ala Ile Val Ser Val Phe Tyr Ala Ser Gly   60

181 TAC ACT CCC GAC GAG ATG TTA AAA CTC CTG AAA GAG GTA AAC TGG CTC AAA CTT TTT AAG  240
 61 Tyr Thr Pro Asp Glu Met Leu Lys Leu Leu Lys Glu Val Asn Trp Leu Lys Leu Phe Lys   80

241 TTC AAA ACA CCG AAA ATG GGC TTA ATG GGG TGG GCA GAG TTT GCA GCT GAA AAA           300
 81 Phe Lys Thr Pro Lys Met Gly Leu Met Gly Trp Ala Glu Phe Ala Ala Glu Lys          100

301 GAG CTC GGA GTT AAG AGG CTG AAG CTC AAC GAC ATA CCA ACC TAT CTT TGC TCG GCG GAT  360
101 Glu Leu Gly Val Lys Arg Leu Lys Leu Asn Asp Ile Pro Thr Tyr Leu Cys Ser Ala Asp  120

361 CTG TAC ACG GGA AAG GCT CTT TAC TTC GAC GGT AGA GGT TTA ATT CCC GTG CTT CTC GGA  420
121 Leu Tyr Thr Gly Lys Ala Leu Tyr Phe Asp Gly Arg Gly Leu Ile Pro Val Leu Leu Gly  140

421 AGT TGT TCC ATA CCC GGG ATT TTT GAA CCA GTT TTT GAG TAC GAG AAT TTT CTA CTT GTT GAC  480
141 Ser Cys Ser Ile Pro Gly Ile Phe Glu Pro Val Phe Glu Tyr Glu Asn Phe Leu Leu Val Asp  160

481 GGA GGT ATA GTG AAC CTG AAC AAC CTG GAA CCT TTG GAA AAG TTC AAA CCC ATA ATC  540
161 Gly Gly Ile Val Asn Leu Asn Asn Leu Glu Pro Leu Glu Lys Phe Lys Pro Ile Ile      180

541 GGG GTA GAT GTG CTT CCC ATA ACT CAA GAA AGA AAG ATT AAA AAT ATA CTC CAC ATC CTT  600
181 Gly Val Asp Val Leu Pro Ile Thr Gln Glu Arg Lys Ile Lys Asn Ile Leu His Ile Leu  200

601 ATA AGG AGC TTC TTT CTG GCG GTT CGT TCC AAT TCG GAA AAG AGA AAG GAG TTC TGC AAC  660
201 Ile Arg Ser Phe Phe Leu Ala Val Arg Ser Asn Ser Glu Lys Arg Lys Glu Phe Cys Asn  220

661 GTA GTT ATA GAA CCT CCC CTT GAA TTC TCT CCT CTG GAG TTC CTG GAC GTA AAT AAG GCG GAC GAG  720
221 Val Val Ile Glu Pro Pro Leu Glu Phe Ser Pro Leu Glu Phe Leu Asp Val Asn Lys Ala Asp Glu  240

721 ATA TTC TGC GGG GAT ATG AGA GCA CTT TAA                                          750
241 Ile Phe Cys Gly Asp Met Arg Ala Leu End                                          250
```

FIG.12A
Teredinibacter - 42L

```
  1 ATG CCA GCT AAT GAC TCA CCC ACG ATC GAC TTT AAT CCT CGC GGC ATT CTT CGC AAC GCT  60
  1 Met Pro Ala Asn Asp Ser Pro Thr Ile Asp Phe Asn Pro Arg Gly Ile Leu Arg Asn Ala  20

61 CAC GCA CAG GTT ATT TTA GGG ACT TCC GGC TTG CGC AAA GCG TTT GCA AAA CGC ACG CAC 120
 21 His Ala Gln Val Ile Leu Gly Thr Ser Gly Leu Arg Lys Ala Phe Ala Lys Arg Thr His  40

121 AAG AGC TAC CTC AGC ACT GCC CAA TGG CTG GAG CTC GAT GCC AAC GGA GTT ACC TTG 180
 41 Lys Ser Tyr Leu Ser Thr Ala Gln Trp Leu Glu Leu Asp Ala Gly Val Thr Leu  60

181 GCC GGA GAG CTT AAC ACA GCG CCT GCA ACT GCA TCC TCC CAC CCG GCG CAC AAG AAC 240
 61 Ala Gly Glu Leu Asn Thr Ala Pro Ala Thr Ala Ser Ser His Pro Ala His Lys Asn  80

241 ACT CTG GTT ATT GTG CTG CAC GGC GAA TGG TCC AGC CAG TCG GCC TAT GGA ACC TCC 300
 81 Thr Leu Val Ile Val Leu His Gly Glu Trp Ser Ser Gln Ser Ala Tyr Ala Thr Ser 100

301 GCT GGC ACG CTT GAC AAT GGG TTC GAC ACT TTT CGC CTT AAT TTT CGC GAT CAC 360
101 Ala Gly Ser Thr Leu Asp Asn Gly Phe Asp Thr Phe Arg Leu Asn Phe Arg Asp His 120

361 GGC GAC ACC TAC CAC CAC TTA AAC CGC GGC ATA TTT AAC TCA CTG ATT GAC GAA GTA GTG 420
121 Gly Asp Thr Tyr His His Leu Asn Arg Gly Ile Phe Asn Ser Leu Ile Asp Glu Val Val 140

421 GGC GCA GTC AAA GCC ATC CAG CAG CAA TAC GAC AAG TAT TGC CTG ATG GGG TTC 480
141 Gly Ala Val Lys Ala Ile Gln Gln Gln Tyr Asp Lys Tyr Cys Leu Met Gly Phe 160

481 TCA CTG GGT GGG AAC TTT GCC TTG CGC GTG GTG CGG GAA CAG CAT CTC GCT AAA CCG 540
161 Ser Leu Gly Gly Asn Phe Ala Leu Arg Val Val Arg Glu Gln His Leu Ala Lys Pro 180

541 CTA GCG GGC GTG GCG GTA TGC CCG GTA CTC GCC GAC CCC GCA CAC ACC ATG GCC CTA 600
181 Leu Ala Gly Val Ala Val Cys Pro Val Leu Ala Asp Pro Ala His Thr Met Ala Leu 200

601 AAC CGA GGT GCG TTT TTC TAC CGC TAT TTT GCG CAT AAA TGG AAG TCG TTA ACC 660
201 Asn Arg Gly Ala Phe Phe Tyr Arg Tyr Phe Ala His Lys Trp Lys Ser Leu Thr 220

661 GCA AAA CTT GCA GCT TTC CCA GAT TAC AAA GAT TTA GGC AAA TAC TCG ATA CAC ACG 720
221 Ala Lys Leu Ala Ala Phe Pro Asp Tyr Lys Asp Leu Gly Lys Tyr Ser Ile His Thr 240
```

FIG.12B
Teredinibacter - 42L

```
721  CTT GAT GAG TTA AAC AAC TAT TTC ATT CCC CGC TAC ACC GGC TTC AAC TCA GTC TCC GAA   780
241  Leu Asp Glu Leu Asn Asn Tyr Phe Ile Pro Arg Tyr Thr Gly Phe Asn Ser Val Ser Glu  260
781  TAC TTC AAA AGT TAC ACG CTC ACC CAG AAG CTG GCG TTT CTC AAC TGC CCC AGT TAC       840
261  Tyr Phe Lys Ser Tyr Thr Leu Thr Gln Lys Leu Ala Phe Leu Asn Cys Pro Ser Tyr      280
841  ATT CTG GCA GCT GGC GAC GAC CCA ATA ATT CCA GCA TCC GAC TTT CAG GAC TCC AAG       900
281  Ile Leu Ala Ala Gly Asp Asp Pro Ile Ile Pro Ala Ser Asp Phe Gln Lys Ile Ala Lys  300
901  CCT GCG AAT CTG CAC ATA ACA GTA ACG CAA GGT TCT CAT TGC GCA TAC CTG GAA AAC       960
301  Pro Ala Asn Leu His Ile Thr Val Thr Gln Gly Ser His Cys Ala Tyr Leu Glu Asn      320
961  CTG CAT AAA CCT AGT GCT GCC GAC AAA TAT GCG GTG AAA TTA TTT GGA GCC TGT TGA       1017
321  Leu His Lys Pro Ser Ala Ala Asp Lys Tyr Ala Val Lys Leu Phe Gly Ala Cys End      339
```

FIG. 13A
Archeoglogus fulgidas VC16 - 16MC1

| | | | | | | | | | |
|---|---|---|---|---|---|---|---|---|---|
| ATG Met 1 | CTT Leu | GAT Asp | ATG Met | CCA Pro 5 | ATC Ile | GAC Asp | CCT Pro | GTT Val | TAC Tyr |
| CAG Gln | CTT Leu | GCT Ala | GAG Glu | TAT Tyr 15 | | | | | |
| TTC Phe | AGG Arg | AGT Ser | CTG Leu 20 | CCG Pro | AAG Lys | TTC Phe | TAC Tyr | TCC Ser | TTC Ser 30 | GCC Ala | AGA Arg | GAG Glu | TAC Tyr |
| AGG Arg | GCG Ala | ATA Ile 35 | AAT Asn | CGA Arg | ATA Ile 40 | TAC Tyr | AGA Arg | AAC Asn | ACG Thr | CGG Arg | CAG Gln | CTG Leu | AGC Ser |
| CAG Gln | CAT His | GAG Glu 50 | AGG Arg | GTT Val | GAA Glu | GTT Val | GAG Glu | GAC Asp | GTT Val 60 | AGG Arg | CAG Gln | AAG Lys | GGG Gly |
| AAC Asn | GGA Gly 65 | GAC Asp | ATC Ile | AGA Arg | AGA Arg 70 | AGA Arg | GTC Val | TAC Tyr 75 | TTT Phe | CCC Pro | GAT Asp | AGC Ser | TCC Ser |
| GGT Gly | CTG Leu | GTT Val | TAC Tyr 85 | TAT Tyr | CAC His | TTA Leu | TGC Cys 90 | GGA Gly | GGT Gly | TTT Phe | ATT Ile | TGC Cys 80 | ATC Ile |
| TCG Ser | CAC His | GAC Asp 100 | GCC Ala | TTA Leu | TGC Cys | TAC Tyr | AGA Arg 105 | AYY Ile | GCA Ala | GCG Ala | CTT Leu 110 | CAC His | TCA Ser | AAC Asn | ACC Thr |
| GTA Val | GTC Val | TCC Ser 115 | GTG Val | GAT Asp | TGC Cys | TAC Tyr 120 | AGG Arg | CTC Leu | GCT Ala | CCT Pro | AAG Lys 125 | TGG Trp | TTT Phe | AAG Lys | GCT Ala |
| CCA Ala | GTT Val | TAT Tyr 130 | CAT His | AGG Arg | ATT Ile | GAT Asp | AGG Arg 135 | AGC Ser | ACC Thr | GAC Asp | ACC Thr 140 | AAG Lys | ATC Ile | ATC Ile | GTT Val |
| GAG Glu | GAG Glu 145 | CTG Leu | AGG Arg | AAT Asn | ATT Ile 150 | CTT Leu | TCA Ser | AAA Lys 155 | TTC Phe | ATA Ile | TCA Ser | GAC Asp | AGT Ser | GGG Gly | GAC Asp |
| GCG Ala 160 | GGA Gly 165 | CGG Arg | AAT Asn | CTT Leu | GCC Ala | CCG Pro 170 | GCG Ala | GCC Ala | ATG Met | TCA Ser 175 | ATA Ile | TCA Ser | ATG Met | AGA Arg | AGC Ser | GAC Asp | AGC Ser |

FIG. 13B
*Archeoglogus fulgidas VC16 - 16MC1*

| GGA Gly | GAA Glu | GAT Asp | TTC Phe 180 | ATA Ile | AAG Lys | CAT His 185 | GAA Gln | CTA Leu | ACT Ile 190 | TAC Tyr | CCC Pro | GTT Val | GTG Val | AAC Asn |
| TTT Phe | GTA Val 195 | GCC Ala | CCC Pro | ACA Thr | CCA Pro 200 | TCG Ser | CTT Leu | GAG Glu | TTT Phe 205 | GGA Gly | GAG Glu | GGG Gly | CTG Leu | TGG Trp |
| ATT Ile | CTC Leu 210 | GAC Asp | CAG Gln | AAG Lys | ATA Ile 215 | ATG Met | AGT Ser | TGG Trp | TTC Phe 230 | TTC Phe | CCG Ser | GAG Glu | TAC Tyr | TTC Phe | TCC Ser |
| AGA Arg 235 | GAG Glu | GAA Glu | GAT Asp | AAG Lys 240 | AAG Lys | AGT Ser | CTC Leu 245 | TCC Ser | GTA Val | CAG Gln | TTT Phe | GGG Gly | GAC Asp |
| CTT Leu | GAT Asp | AAC Asn | CTA Leu 255 | CCT Pro | CCC Pro | CTG Leu | ATC Ile 260 | GCC Ala | ACC Thr | ATC Ile 250 | GAA Glu | AGA Arg | TAC Tyr | GAC Asp | CCG Pro |
| CTG Leu | AGA Arg | GAT Asp 270 | GAA Glu | GTT Val | GGA Gly | TTC Phe 275 | ATA Ile | CAG Gln 280 | ATG Met | CTG Leu | AGA Arg | CAC His | GCC Ala | GGT Gly |
| GTT Val | GAG Glu | GCG Ala | AGC Ser | GTC Val | AGA Arg | TAC Tyr | AGA Arg | TAC Tyr | GGC Gly | GTG Val | GTG Val 295 | CTT Leu | CAC His | GGA Gly | ATC Ile |
| AAT Asn | TAC Tyr | TAT Tyr 300 | CCC Pro | CTG Leu | AAG Lys | CTG Leu 305 | AAG Lys | GCT Ala | AGG Arg | GAT Asp 310 | GCG Ala | ATA Ile | AAC Asn | CAG Gln | ATT Ile |
| GCC Ala 315 | GCT Ala | CTT Leu | CTT leu | GTG Val 320 | TTC Phe | GAC Asp | TAG |

FIG. 14A
Sulfolobus Solfatarious P1 8LC1

```
ATG CCC CTA GAT CCT AGA ATT AAA AAG TTA CTA GAA TCA GCT CTT ACT
Met Pro Leu Asp Pro Arg Ile Lys Lys Leu Leu Glu Ser Ala Leu Thr
 1           5               10              15

ATA CCA GGT AAA GCC GTA CCA GAG GAA GTC GTT ATA AAG AGA ATA TTT
Ile Pro Gly Lys Ala Val Pro Glu Glu Val Val Ile Lys Arg Ile Phe
         20          25              30

CAA TTA GCG TCG GCT GCA CCC AAA ACC GAA GTT GAA GTA GAT GAA GGC
Gln Leu Ala Ser Ala Ala Pro Lys Thr Glu Val Glu Val Asp Glu Gly
             35          40              45

ATA AAA CCA ATA AGT AGC GGT CCT GAT AAT TGC CCT AAT TTT CTT GGC
Ile Lys Pro Ile Ser Ser Gly Pro Asp Asn Cys Pro Asn Phe Leu Gly
     50              55          60              65

CCG AAG AGC GGT TTT CCT GAT GTG TGC AAT CCT AAT AAC TTA CAT TGT
Pro Lys Ser Gly Phe Pro Asp Val Cys Asn Pro Asn Asn Leu His Cys
         70              75              80

GGT ATA GCG GGA TCT GAC GTA TGG TAT TAT TTT TCA CCT GAC CTA GGA
Gly Ile Ala Gly Ser Asp Val Trp Tyr Tyr Phe Ser Pro Asp Leu Gly
         85              90              95

ATT ACA AAT GCG TAC GTT GTA GTG TCA ATC TTT AAG ATG GAC TCA AGG
Ile Thr Asn Ala Tyr Val Val Val Ser Ile Phe Lys Met Asp Ser Arg
    100             105             110

GCT CCA GAA TGG AAG TAT TTA GAT TTT AAT GGA AGT ATT GAT GCT AGG
Ala Pro Glu Trp Lys Tyr Leu Asp Phe Asn Gly Ser Ile Asp Ala Arg
        115             120             125

ACT AAT TGG GTT TAT AAG TAT AAC AAT TTT GAT GGA GGA AAG AAG GAC
Thr Asn Trp Val Tyr Lys Tyr Asn Asn Phe Asp Gly Gly Lys Lys Asp
        130             135             140

GTT GCG ATT GCG AGT GAT GGA GGG GCT AAT TTG GCA AAG ATG GTT GTA
Val Ala Ile Ala Ser Asp Gly Gly Ala Asn Leu Ala Lys Met Val Val
145             150             155             160
```

FIG. 14B
Sulfolobus Solfatarious P1 8LC1

```
GCT CTT CTT TCA AAG GGT AAA ATT AAT TTG AAG TAT CAA ATA CTG GTT
Ala Leu Leu Ser Lys Gly Lys Ile Asn Leu Lys Tyr Gln Ile Leu Val
            165                 170                 175
TAC CCA GCG GTA AGT TTA GAT AAC GTT TCA AGA TCC ATG ATA GAG TAC
Tyr Pro Ala Val Ser Leu Asp Asn Val Ser Arg Ser Met Ile Glu Tyr
            180                 185                 190
TCT GAT GGG TTC TTC CTT ACC AGA CAT ATA GAG TGG TTC GGT TCT
Ser Asp Gly Phe Phe Leu Thr Arg His Ile Glu Trp Phe Gly Ser
    195                 200                 205
CAA TAC TTA CGA AGC GCA CCT GAT CTA TTG TTT AGG TTC TCT CCA
Gln Tyr Leu Arg Ser Ala Pro Asp Leu Leu Phe Arg Phe Ser Pro
210                 215                 220
ATT CTG GCG CAA GAT TTC AAC GGA TTA CCT CAA GCC TTC ATA ACA
Ile Leu Ala Gln Asp Phe Asn Gly Leu Pro Gln Ala Leu Ile Thr
225                 230                 235                 240
GCA GAA TAC GAT CCA GTA CGA AGG GAT CAA GGA GCG TAT TTT AAA
Ala Glu Tyr Asp Pro Val Arg Arg Asp Gln Gly Ala Tyr Phe Lys
245                 250                 255
CTA CTA CAA GCT GGA GTC TCA AGT ACT GTT AGA GAG AAC GTT
Leu Leu Gln Ala Gly Val Ser Ser Thr Val Arg Glu Asn Val
    260                 265                 270
ATA CAC TTC TTC CTC TTC TTT CCG TTG ATG CAA GGA AGA GAT
Ile His Phe Phe Leu Phe Phe Pro Leu Met Gln Gly Arg Asp
    275                 280                 285
GCT ATA GGT CTG ATA GGG TCT GTG TTA TCT CGA GTA TTT TAT AAA
Ala Ile Gly Lru Ile Gly Ser Val Leu Ser Arg Val Phe Tyr Asp Lys
290                 295                 300
ATT
Ile
305
```

NUCLEIC ACIDS ENCODING ESTERASES AND METHODS OF MAKING AND USING THEM

RELATED APPLICATIONS

This application is a continuation-in-part of and claims the benefit of U.S. application Ser. No. 09/382,242, filed Aug. 24, 1999, now abandoned; which is a continuation of U.S. application Ser. No. 08/602,359, filed Feb. 16, 1996, now issued U.S. Pat. 5,942,430, all which are herein incorporated by reference in their entirety.

FIELD OF THE INVENTION

This invention relates generally to enzymes, polynucleotides encoding the enzymes, the use of such polynucleotides and polypeptides, and more specifically to enzymes having esterase activity.

BACKGROUND

Many esterases are known and have been discovered in a broad variety of organisms, including bacteria, yeast and higher animals and plants. A principal example of esterases are the lipases, which are used in the hydrolysis of lipids, acidolysis (replacement of an esterified fatty acid with a free fatty acid) reactions, transesterification (exchange of fatty acids between triglycerides) reactions, and in ester synthesis. The major industrial applications for lipases include: the detergent industry, where they are employed to decompose fatty materials in laundry stains into easily removable hydrophilic substances; the food and beverage industry where they are used in the manufacture of cheese, the ripening and flavoring of cheese, as antistaling agents for bakery products, and in the production of margarine and other spreads with natural butter flavors; in waste systems; and in the pharmaceutical industry where they are used as digestive aids.

The polynucleotides and polypeptides of the present invention have been identified as esterases as a result of their enzymatic activity.

The publications discussed herein are provided solely for their disclosure prior to the filing date of the present application. Nothing herein is to be construed as an admission that the invention is not entitled to antedate such disclosure by virtue of prior invention.

SUMMARY OF THE INVENTION

The invention provides an isolated nucleic acid having a sequence as set forth in SEQ ID Nos.: 23, 24, 25, 26, 27, 28, 29, 30, 31, 32 and variants thereof having at least 50% sequence identity to SEQ ID Nos.: 23, 24, 25, 26, 27, 28, 29, 30, 31, 32 and encoding polypeptides having esterase activity.

One aspect of the invention is an isolated nucleic acid having a sequence as set forth in SEQ ID No.s: 23, 24, 25, 26, 27, 28, 29, 30, 31, 32 (hereinafter referred to as "Group A nucleic acid sequences"), sequences substantially identical thereto, and sequences complementary thereto.

Another aspect of the invention is an isolated nucleic acid including at least 10 consecutive bases of a sequence as set forth in Group A nucleic acid sequences, sequences substantially identical thereto, and the sequences complementary thereto.

In yet another aspect, the invention provides an isolated nucleic acid encoding a polypeptide having a sequence as set forth in SEQ ID Nos.: 33, 34, 35, 36, 37, 38, 39, 40, 41, 42 and variants thereof encoding a polypeptide having esterase activity and having at least 50% sequence identity to such sequences.

Another aspect of the invention is an isolated nucleic acid encoding a polypeptide or a functional fragment thereof having a sequence as set forth in SEQ ID No.s: 33, 34, 35, 36, 37, 38, 39, 40, 41, 42 (hereinafter referred to as "Group B amino acid sequences"), and sequences substantially identical thereto.

Another aspect of the invention is an isolated nucleic acid encoding a polypeptide having at least 10 consecutive amino acids of a sequence as set forth in Group B amino acid sequences, and sequences substantially identical thereto.

In yet another aspect, the invention provides a purified polypeptide having a sequence as set forth in Group B amino acid sequences, and sequences substantially identical thereto.

Another aspect of the invention is an isolated or purified antibody that specifically binds to a polypeptide having a sequence as set forth in Group B amino acid sequences, and sequences substantially identical thereto.

Another aspect of the invention is an isolated or purified antibody or binding fragment thereof, which specifically binds to a polypeptide having at least 10 consecutive amino acids of one of the polypeptides of Group B amino acid sequences, and sequences substantially identical thereto.

Another aspect of the invention is a method of making a polypeptide having a sequence as set forth in Group B amino acid sequences, and sequences substantially identical thereto. The method includes introducing a nucleic acid encoding the polypeptide into a host cell, wherein the nucleic acid is operably linked to a promoter, and culturing the host cell under conditions that allow expression of the nucleic acid.

Another aspect of the invention is a method of making a polypeptide having at least 10 amino acids of a sequence as set forth in Group B amino acid sequences, and sequences substantially identical thereto. The method includes introducing a nucleic acid encoding the polypeptide into a host cell, wherein the nucleic acid is operably linked to a promoter, and culturing the host cell under conditions that allow expression of the nucleic acid, thereby producing the polypeptide.

Another aspect of the invention is a method of generating a variant including obtaining a nucleic acid having a sequence as set forth in Group A nucleic acid sequences, sequences substantially identical thereto, sequences complementary to the sequences of Group A nucleic acid sequences, fragments comprising at least 30 consecutive nucleotides of the foregoing sequences, and changing one or more nucleotides in the sequence to another nucleotide, deleting one or more nucleotides in the sequence, or adding one or more nucleotides to the sequence.

Another aspect of the invention is a computer readable medium having stored thereon a sequence as set forth in Group A nucleic acid sequences, and sequences substantially identical thereto, or a polypeptide sequence as set forth in Group B amino acid sequences, and sequences substantially identical thereto.

Another aspect of the invention is a computer system including a processor and a data storage device wherein the data storage device has stored thereon a sequence as set forth in Group A nucleic acid sequences, and sequences substantially identical thereto, or a polypeptide having a sequence as set forth in Group B amino acid sequences, and sequences substantially identical thereto.

Another aspect of the invention is a method for comparing a first sequence to a reference sequence wherein the first sequence is a nucleic acid having a sequence as set forth in Group A nucleic acid sequences, and sequences substantially identical thereto, or a polypeptide code of Group B amino acid sequences, and sequences substantially identical thereto. The method includes reading the first sequence and the reference sequence through use of a computer program which compares sequences; and determining differences between the first sequence and the reference sequence with the computer program.

Another aspect of the invention is a method for identifying a feature in a sequence as set forth in Group A nucleic acid sequences, and sequences substantially identical thereto, or a polypeptide having a sequence as set forth in Group B amino acid sequences, and sequences substantially identical thereto, including reading the sequence through the use of a computer program which identifies features in sequences; and identifying features in the sequence with the computer program.

Another aspect of the invention is an assay for identifying fragments or variants of Group B amino acid sequences, and sequences substantially identical thereto, which retain the enzymatic function of the polypeptides of Group B amino acid sequences, and sequences substantially identical thereto. The assay includes contacting the polypeptide of Group B amino acid sequences, sequences substantially identical thereto, or polypeptide fragment or variant with a substrate molecule under conditions which allow the polypeptide fragment or variant to function, and detecting either a decrease in the level of substrate or an increase in the level of the specific reaction product of the reaction between the polypeptide and substrate thereby identifying a fragment or variant of such sequences.

BRIEF DESCRIPTION OF THE DRAWINGS

The following drawings are illustrative of embodiments of the invention and are not meant to limit the scope of the invention as encompassed by the claims.

FIG. 5 is an illustration of the full-length DNA (SEQ ID NO:23) and corresponding deduced amino acid sequence (SEQ ID NO:33) of *Staphylothermus marinus* F1-12LC of the present invention. Sequencing was performed using a 378 automated DNA sequencer (Applied Biosystems, Inc.) for all sequences of the present invention.

FIGS. 6A and 6B are an illustration of the full-length DNA (SEQ ID NO:24) and corresponding deduced amino acid sequence (SEQ ID NO:34) of Pyrodictium TAGI 1-17LC.

FIGS. 7A and 7B are an illustration of the full-length DNA (SEQ ID NO:25) and corresponding deduced amino acid sequence (SEQ ID NO:35) of *Archaeoglobus venificus* SNP6-24LC.

FIG. 8 is an illustration of the full-length DNA (SEQ ID NO:26) and corresponding deduced amino acid sequence (SEQ ID NO:36) of *Aquifex pyrophilus*-28LC.

FIGS. 9A and 9B are an illustration of the full-length DNA (SEQ ID NO:27) and corresponding deduced amino acid sequence (SEQ ID NO: 37) of M11TL-29L.

FIGS. 10A and 10B are an illustration of the full-length DNA (SEQ ID NO:28) and corresponding deduced amino acid sequence (SEQ ID NO:38) of Thermococcus CL-2-30LC.

FIG. 11 is an illustration of the full-length DNA (SEQ ID NO:29) and corresponding deduced amino acid sequence (SEQ ID NO:39) of Aquifex VF5-34LC.

FIGS. 12A and 12B are an illustration of the full-length DNA (SEQ ID NO:30) and corresponding deduced amino acid sequence (SEQ ID NO:40) of Teredinibacter-42L.

FIGS. 13A and 13B are an illustration of the full-length DNA (SEQ ID NO:31) and corresponding deduced amino acid sequence (SEQ ID NO:41) of *Archaeoglobus fulgidus* VC16-16MC.

FIGS. 14A and 14B are an illustration of the full-length DNA (SEQ ID NO:32) and corresponding deduced amino acid sequence (SEQ ID NO:42) of *Sulfolobus solfataricus* P1-8LC.

DETAILED DESCRIPTION OF THE INVENTION

Figure 1:
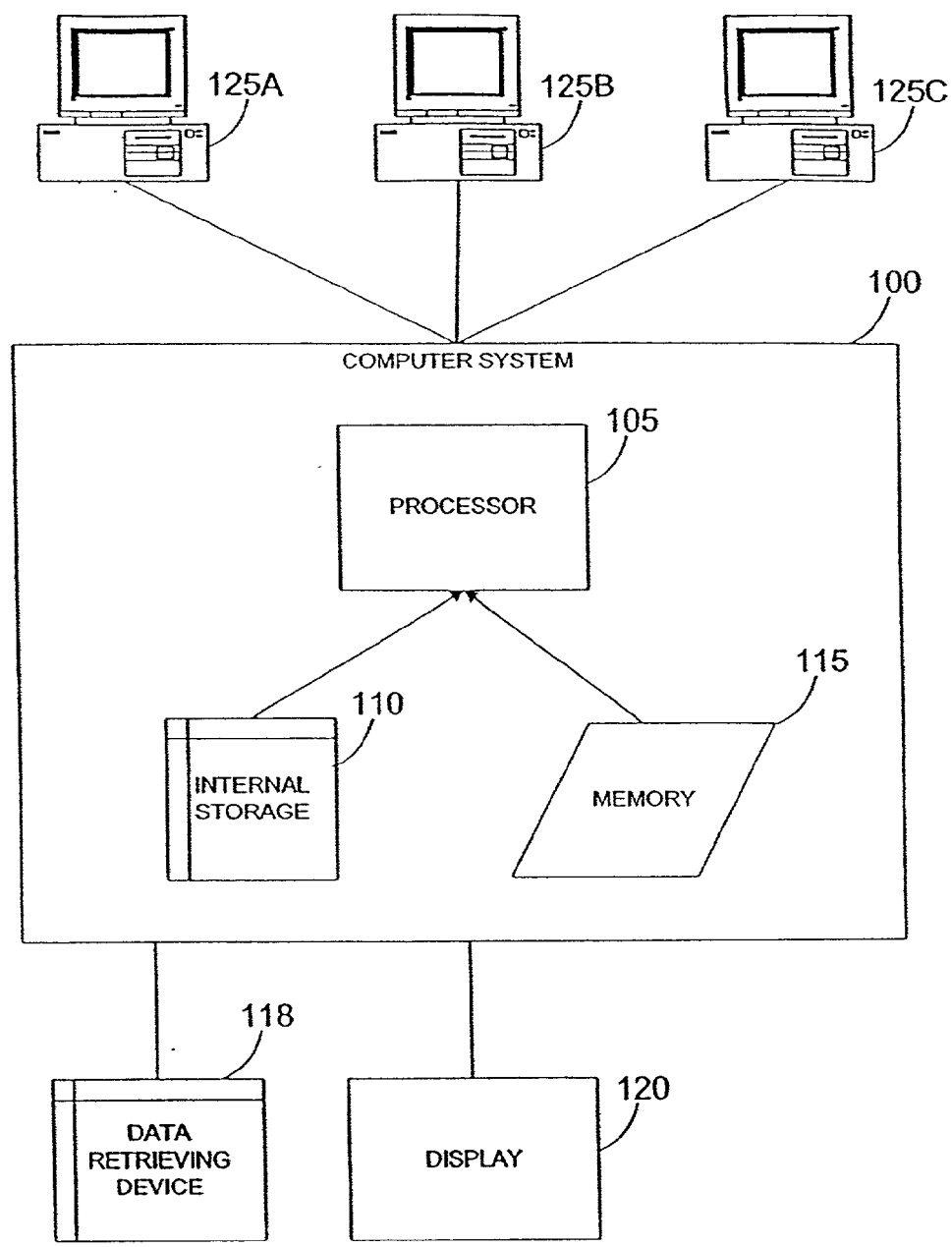
FIG. 1 is a block diagram of a computer system.

The present invention relates to esterases and polynucleotides encoding them. As used herein, the term "esterase" encompasses enzymes having hydrolase activity, for example, enzymes capable of hydrolyzing ester groups to organic acids and alcohols.

The polynucleotides of the invention have been identified as encoding polypeptides having esterase activity.

Definitions

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin.

A "coding sequence of" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons).

"Amino acid" or "amino acid sequence" as used herein refer to an oligopeptide, peptide, polypeptide, or protein sequence, or to a fragment, portion, or subunit of any of these, and to naturally occurring or synthetic molecules.

The term "polypeptide" as used herein, refers to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid sidechains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphytidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Creighton, T. E., *Proteins—Structure and Molecular Properties 2nd Ed.*, W. H. Freeman and Company, New York (1993); *Posttranslational Covalent Modification of Proteins*, B. C. Johnson, Ed., Academic Press, New York, pp. 1-12 (1983)).

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least $10^4$-$10^6$ fold. However, the term "purified" also includes nucleic acids which have been purified from the remainder of the genomic DNA or from other sequences in a library or other environment by at least one order of magnitude, typically two or three orders, and more typically four or five orders of magnitude.

As used herein, the term "recombinant" means that the nucleic acid is adjacent to a "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one embodiment, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., *J. Am. Chem. Soc.*, 85:2149-2154, 1963) (See also Stewart, J. M. and Young, J. D., *Solid Phase Peptide Synthesis, 2nd Ed.*, Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, *Proc. Natl. Acad. Sci., USA,* 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A promoter sequence is "operably linked to" a coding sequence when RNA polymerase which initiates transcription at the promoter will transcribe the coding sequence into mRNA.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion, gel electrophoresis may be performed to isolate the desired fragment.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acids or polypeptides, refers to two or more sequences that have at least 50%, 60%, 70%, 80%, and in some aspects 90-95% nucleotide or amino acid residue identity, when compared and aligned for maximum correspondence, as measured using one of the known sequence comparison algorithms or by visual inspection. Typically, the substantial identity exists over a region of at least about 100 residues, and most commonly the sequences are substantially identical over at least about 150-200 residues. In some embodiments, the sequences are substantially identical over the entire length of the coding regions.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucin, valine, leucine, or methionine, for another, or substitution of one polar amino acid for another, such as substitution of arginine for lysine, glutamic acid for aspartic acid or glutamine for asparagine). One or more amino acids can be deleted, for example, from an esterase polypeptide, resulting in modification of the structure of the polypeptide, without significantly altering its biological activity. For example, amino- or carboxyl-terminal amino acids that are not required for esterase biological activity can be removed. Modified polypeptide sequences of the invention can be assayed for esterase biological activity by any number of methods, including contacting the modified polypeptide sequence with an esterase substrate and determining whether the modified polypeptide decreases the amount of specific substrate in the assay or increases the bioproducts of the enzymatic reaction of a functional esterase polypeptide with the substrate.

"Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 85% identical. Fragments which have different three dimensional structures as the naturally occurring protein are also included. An example of this, is a "pro-form" molecule, such as a low activity proprotein that can be modified by cleavage to produce a mature enzyme with significantly higher activity.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 ng/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain the biological activity of an esterase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof Enzymes are highly selective catalysts. Their hallmark is the ability to catalyze reactions with exquisite stereo-, regio-, and chemo-selectivities that are unparalleled in conventional synthetic chemistry. Moreover, enzymes are remarkably versatile. They can be tailored to function in organic solvents, operate at extreme pHs (for example, high pHs and low pHs) extreme temperatures (for example, high temperatures and low temperatures), extreme salinity levels (for example, high salinity and low salinity), and catalyze reactions with compounds that are structurally unrelated to their natural, physiological substrates.

Enzymes are reactive toward a wide range of natural and unnatural substrates, thus enabling the modification of virtually any organic lead compound. Moreover, unlike traditional chemical catalysts, enzymes are highly enantio- and regio-selective. The high degree of functional group specificity exhibited by enzymes enables one to keep track of each reaction in a synthetic sequence leading to a new active compound. Enzymes are also capable of catalyzing many diverse reactions unrelated to their physiological function in nature. For example, peroxidases catalyze the oxidation of phenols by hydrogen peroxide. Peroxidases can also catalyze hydroxylation reactions that are not related to the native function of the enzyme. Other examples are proteases which catalyze the breakdown of polypeptides. In organic solution some proteases can also acylate sugars, a function unrelated to the native function of these enzymes.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds.

Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods. (For further teachings on modification of molecules, including small molecules, see PCT/US94/09174, herein incorporated by reference in its entirety).

In one aspect, the present invention provides a non-stochastic method termed synthetic gene reassembly, that is somewhat related to stochastic shuffling, save that the nucleic acid building blocks are not shuffled or concatenated or chimerized randomly, but rather are assembled non-stochastically.

The synthetic gene reassembly method does not depend on the presence of a high level of homology between polynucleotides to be shuffled. The invention can be used to non-stochastically generate libraries (or sets) of progeny molecules comprised of over $10^{100}$ different chimeras. Conceivably, synthetic gene reassembly can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment of the invention, the annealed building pieces are treated with an enzyme, such as a ligase (e.g., T4 DNA ligase) to achieve covalent bonding of the building pieces.

In a another embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. The esterases of the present invention can be mutagenized in accordance with the methods described herein.

Thus according to one aspect of the invention, the sequences of a plurality of progenitor nucleic acid templates (e.g., polynucleotides of Group A nucleic acid sequences) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and preferably at almost all of the progenitor templates. Even more preferably still a serviceable demarcation point is an area of homology that is shared by all of the progenitor templates.

In a one embodiment, the gene reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another embodiment, the method provides that the gene reassembly process is performed systematically, for example to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant gene reassembly invention, the progeny molecules generated preferably comprise a library of finalized chimeric nucleic acid molecules having an overall assembly order that is chosen by design. In a particularly embodiment, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In a preferred instance, the recombination is facilitated by, or occurs at, areas of homology between the man-made, intron-containing gene and a nucleic acid, which serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic gene reassembly method of the invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one embodiment, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect the invention described herein is directed to the use of repeated cycles of reductive reassortment, recombination and selection which allow for the directed molecular evolution of highly complex linear sequences, such as DNA, RNA or proteins thorough recombination.

In vivo shuffling of molecules is useful in providing variants and can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another embodiment, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides (e.g., hybrid esterases). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g. high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by the polynucleotides of the invention include, but are not limited to, hydrolases, such as esterases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e. the type of bond on which the hydrolase acts and the temperature at which the hydrolase functions. Thus, for example, the hydrolase may be screened to ascertain those chemical functionalities which distinguish the hybrid hydrolase from the original hydrolases, such as: (a) amide (peptide bonds), i.e., proteases, (b) ester bonds, i.e., esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as Eubacteria and Archaebacteria, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of E. coli. This f-factor of E. coli is a plasmid which affect high-frequency transfer of itself during conjugation and is ideal to achieve and stably propagate large DNA fragments, such as gene clusters from mixed microbial samples. A particularly preferred embodiment is to use cloning vectors, referred to as "fosmids" or bacterial artificial chromosome (BAC) vectors. These are derived from E. coli f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in Sambrook et AL, *Molecular Cloning: A Laboratory Manual, 2nd Ed.*, Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a one embodiment, the invention relates to a method for producing a biologically active hybrid polypeptide and screening such a polypeptide for enhanced activity by:

1) introducing at least a first polynucleotide in operable linkage and a second polynucleotide in operable linkage, said at least first polynucleotide and second polynucleotide sharing at least one region of partial sequence homology, into a suitable host cell;

2) growing the host cell under conditions which promote sequence reorganization resulting in a hybrid polynucleotide in operable linkage;

3) expressing a hybrid polypeptide encoded by the hybrid polynucleotide;

4) screening the hybrid polypeptide under conditions which promote identification of enhanced biological activity; and 5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

As representative examples of expression vectors which may be used, there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:

a) Primers that include a poly-A head and poly-T tail which when made single-stranded would provide orientation can be utilized. This is accomplished by having the first few bases of the primers made from RNA and hence easily removed RNAseH.

b) Primers that include unique restriction cleavage sites can be utilized. Multiple sites, a battery of unique sequences, and repeated synthesis and ligation steps would be required.

c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by:

1) The use of vectors only stably maintained when the construct is reduced in complexity.

2) The physical recovery of shortened vectors by physical procedures. In this case, the cloning vector would be recovered using standard plasmid isolation procedures and size fractionated on either an agarose gel, or column with a low molecular weight cut off utilizing standard procedures.

3) The recovery of vectors containing interrupted genes which can be selected when insert size decreases.

4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, viron, or other predetermined compound or structure.

The polypeptides that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine (See Sun and Hurley, (1992); an N-acelylated or deacetylated 4'-fluro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[α]anthracene ("BMA"), tris(2,3-dibromopropyl) phosphate ("Tris-BP"), 1,2-dibromo-3-chloropropane ("DBCP"), 2-bromoacrolein (2BA), benzo[α]pyrene-7,8-dihydrodiol-9-10-epoxide ("BPDE"), a platinum(II) halogen salt, N-hydroxy-2-amino-3-methylimidazol[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (gene site saturated mutagenesis (GSSM)). The oligos used are comprised contiguously of a first homologous sequence, a degenerate N,N,N sequence, and preferably but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,N cassette) is used for subjecting each original codon in a parental polynucleotide template to a full range of codon substitutions. In another aspect, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions, and/or substitutions.

In a particular exemplification, it is possible to simultaneously mutagenize two or more contiguous amino acid positions using an oligo that contains contiguous N,N,N triplets, i.e. a degenerate $(N,N,N)_n$ sequence.

In another aspect, the present invention provides for the use of degenerate cassettes having less degeneracy than the N,N,N sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, N,N,G/T, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in a preferred embodiment of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject every or a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette is preferably about 1-500 bases in length) in defined polynucleotide sequence to be mutagenized (wherein the sequence to be mutagenized is preferably from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include a whole gene, pathway, cDNA, an entire open reading frame (ORF), and entire promoter, enhancer, repressor/transactivator, origin of replication, intron, operator, or any polynucleotide functional group. Generally, a "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

One aspect of the invention is an isolated nucleic acid comprising one of the sequences of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of a Group A nucleic acid sequence (or the sequences complementary thereto). The isolated, nucleic acids may comprise DNA, including cDNA, genomic DNA, and synthetic DNA. The DNA may be double-stranded or single-stranded, and if single stranded may be the coding strand or non-coding (anti-sense) strand. Alternatively, the isolated nucleic acids may comprise RNA.

As discussed in more detail below, the isolated nucleic acids of one of the Group A nucleic acid sequences, and sequences substantially identical thereto, may be used to prepare one of the polypeptides of a Group B amino acid sequence, and sequences substantially identical thereto, or fragments comprising at least 5, 10, 15, 20, 25, 30, 35, 40, 50, 75, 100, or 150 consecutive amino acids of one of the polypeptides of Group B amino acid sequences, and sequences substantially identical thereto.

Accordingly, another aspect of the invention is an isolated nucleic acid which encodes one of the polypeptides of Group B amino acid sequences, and sequences substantially identical thereto, or fragments comprising at least 5, 10, 15, 20, 25, 30, 35, 40, 50, 75, 100, or 150 consecutive amino acids of one of the polypeptides of the Group B amino acid sequences. The coding sequences of these nucleic acids may be identical to one of the coding sequences of one of the nucleic acids of Group A nucleic acid sequences, or a fragment thereof or may be different coding sequences which encode one of the polypeptides of Group B amino acid sequences, sequences substantially identical thereto, and fragments having at least 5, 10, 15, 20, 25, 30, 35, 40, 50, 75, 100, or 150 consecutive amino acids of one of the polypeptides of Group B amino acid sequences, as a result of the redundancy or degeneracy of the genetic code. The genetic code is well known to those of skill in the art and can be obtained, for example, on page 214 of B. Lewin, *Genes VI*, Oxford University Press, 1997, the disclosure of which is incorporated herein by reference.

The isolated nucleic acid which encodes one of the polypeptides of Group B amino acid sequences, and sequences substantially identical thereto, may include, but is not limited to: only the coding sequence of one of Group A nucleic acid sequences, and sequences substantially identical thereto, and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only the coding sequence for the polypeptide as well as a polynucleotide which includes additional coding and/or non-coding sequence.

Alternatively, the nucleic acid sequences of Group A nucleic acid sequences, and sequences substantially identical thereto, may be mutagenized using conventional techniques, such as site directed mutagenesis, or other techniques familiar to those skilled in the art, to introduce silent changes into the polynucleotides of Group A nucleic acid sequences, and sequences substantially identical thereto. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of Group B amino acid sequences, and sequences substantially identical thereto. Such nucleotide changes may be introduced using techniques such as site directed mutagenesis, random chemical mutagenesis, exonuclease III deletion, and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto (or the sequences complementary thereto) under conditions of high, moderate, or low stringency as provided herein.

The isolated nucleic acids of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto, or the sequences complementary thereto may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel et al. *Current Protocols in Molecular Biology*, John Wiley 503 Sons, Inc. (1997) and Sambrook et al., *Molecular Cloning: A Laboratory Manual 2nd Ed.*, Cold Spring Harbor Laboratory Press (1989), the entire disclosures of which are incorporated herein by reference.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one embodiment, the amplification reaction may comprise a PCR reaction. PCR protocols are described in Ausubel and Sambrook, supra. Alternatively, the amplification may comprise a ligase chain reaction, 3 SR, or strand displacement reaction. (See Barany, F., "The Ligase Chain Reaction in a PCR World", *PCR Methods and Applications* 1:5-16, 1991; E. Fahy et al., "Self-sustained Sequence Replication (3SR): An Isothermal Transcription-based Amplification System Alternative to PCR", *PCR Methods and Applications* 1:25-33, 1991; and Walker G. T. et al., "Strand Displacement Amplification-an Isothermal in vitro DNA Amplification Technique", *Nucleic Acid Research* 20:1691-1696, 1992, the disclosures of which are incorporated herein by reference in their entireties). In such procedures, the nucleic acids in the sample are contacted with the probes, the amplification reaction is performed, and any resulting amplification product is detected. The amplification product may be detected by performing gel electrophoresis on the reaction products and staining the gel with an interculator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences of Group A nucleic acid sequences, and sequences substantially identical thereto, may also be used in chromosome walking procedures to identify clones containing genomic sequences located adjacent to the sequences of Group A nucleic acid sequences, and sequences substantially identical thereto. Such methods allow the isolation of genes which encode additional proteins from the host organism.

The isolated nucleic acids of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto, or the sequences complementary thereto may be used as probes to identify and isolate related nucleic acids. In some embodiments, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/ml polyriboadenylic acid. Approximately $2\times10^7$ cpm (specific activity $4\text{-}9\times10^8$ cpm/ug) of $^{32}P$ end-labeled oligonucleotide probe are then added to the solution. After 12-16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at $T_m$–10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m=81.5+16.6(\log\ [Na+])+0.41(\text{fraction G+C})-(600/N)$ where N is the length of the probe.

If the hybridization is carried out in a solution containing formamide, the melting temperature may be calculated using the equation: $T_m=81.5+16.6(\log\ [Na+])+0.41(\text{fraction G+C})-(0.63\%\ \text{formamide})-(600/N)$ where N is the length of the probe.

Prehybridization may be carried out in 6×SSC, 5× Denhardt's reagent, 0.5% SDS, 100 μg denatured fragmented salmon sperm DNA or 6×SSC, 5× Denhardt's reagent, 0.5% SDS, 100 μg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the $T_m$. For shorter probes, such as oligonucleotide probes, the hybridization may be conducted at 5-10° C. below the $T_m$. Typically, for hybridizations in 6×SSC, the hybridization is conducted at approximately 68° C. Usually, for hybridizations in 50% formamide containing solutions, the hybridization is conducted at approximately 42° C.

All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v.

AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 97%, at least 95%, at least 90%, at least 85%, at least 80%, at least 70%, at least 65%, at least 60%, at least 55%, or at least 50% homology to a nucleic acid sequence selected from the group consisting of one of the sequences of Group A nucleic acid sequences, and sequences substantially identical thereto, or fragments comprising at least about 10, 15, 20, 25, 30, 35, 40, 50, 75, 100, 150, 200, 300, 400, or 500 consecutive bases thereof, and the sequences complementary thereto. Homology may be measured using the alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of Group A nucleic acid sequences or the sequences complementary thereto.

Additionally, the above procedures may be used to isolate nucleic acids which encode polypeptides having at least about 99%, 95%, at least 90%, at least 85%, at least 80%, at least 75%, at least 70%, at least 65%, at least 60%, at least 55%, or at least 50% homology to a polypeptide having the sequence of one of Group B amino acid sequences, and sequences substantially identical thereto, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Another aspect of the invention is an isolated or purified polypeptide comprising the sequence of one of Group A nucleic acid sequences, and sequences substantially identical thereto, or fragments comprising at least about 5, 10, 15, 20, 25, 30, 35, 40, 50, 75, 100, or 150 consecutive amino acids thereof As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Promoters suitable for expressing the polypeptide or fragment thereof in bacteria include the E. coli lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the a factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donor and acceptor sites, transcriptional termination sequences, and 5' flanking non-transcribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli, and the S. cerevisiae TRP1 gene.

In some embodiments, the nucleic acid encoding one of the polypeptides of Group B amino acid sequences, and sequences substantially identical thereto, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof Optionally, the nucleic acid can encode a fusion polypeptide in which one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al Current Protocols in Molecular Biology, John Wiley 503 Sons, Inc. 1997 and Sambrook et al., *Molecular Cloning: A Laboratory Manual 2nd Ed.*, Cold Spring Harbor Laboratory Press (1989), the entire disclosures of which are incorporated herein by reference. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., *Molecular Cloning: A Laboratory Manual, 2nd Ed.*, Cold Spring Harbor, N.Y., (1989), the disclosure of which is hereby incorporated by reference.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH 18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as *E. coli, Streptomyces, Bacillus subtilis, Salmonella typhimurium* and various species within the genera *Pseudomonas, Streptomyces, and Staphylococcus*, fungal cells, such as yeast, insect cells such as *Drosophila* S2 and *Spodoptera Sf*9, animal cells such as CHO, COS or Bowes melanoma, and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (BPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175, 1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of Group B amino acid sequences, and sequences substantially identical thereto, or fragments comprising at least 5, 10, 15, 20, 25, 30, 35, 40, 50, 75, 100, or 150 consecutive amino acids thereof can be synthetically produced by conventional peptide synthesizers. In other embodiments, fragments or portions of the polypeptides may be employed for producing the corresponding full-length polypeptide by peptide synthesis; therefore, the fragments may be employed as intermediates for producing the fill-length polypeptides.

Cell-free translation systems can also be employed to produce one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The invention also relates to variants of the polypeptides of Group B amino acid sequences, and sequences substantially identical thereto, or fragments comprising at least 5, 10, 15, 20, 25, 30, 35, 40, 50, 75, 100, or 150 consecutive amino acids thereof The term "variant" includes derivatives or analogs of these polypeptides. In particular, the variants may differ in amino acid sequence from the polypeptides of Group B amino acid sequences, and sequences substantially identical thereto, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described in Leung, D. W., et al., Technique, 1:11-15, 1989) and Caldwell, R. C. & Joyce G. F., PCR Methods Applic., 2:28-33, 1992, the disclosure of which is incorporated herein by reference in its entirety. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described in Reidhaar-Olson, J. F. & Sauer, R. T., et al., Science, 241:53-57, 1988, the disclosure of which is incorporated herein by reference in its entirety. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in U.S. Pat. No. 5,965,408, filed Jul. 9, 1996, entitled, "Method of DNA Reassembly by Interrupting Synthesis", the disclosure of which is incorporated herein by reference in its entirety.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described in Stemmer, W. P., PNAS, USA, 91:10747-10751, 1994, the disclosure of which is incorporated herein by reference. Briefly, in such procedures a plurality of nucleic acids to be recombined are digested with DNAse to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/µl in a solution of 0.2 mM of each dNTP, 2.2 mM MgCl2, 50 mM KCL, 10 mM Tris HCl, pH 9.0, and 0.1% Triton X-100. 2.5 units of Taq polymerase per 100 µl of reaction mixture is added and PCR is performed using the following regime: 940° C. for 60 seconds, 94° C. for 30 seconds, 50-55° C. for 30 seconds, 72° C. for 30-45 times) and 72° C. for 5 minutes. However, it will be appreciated that these parameters may be varied as appropriate. In some embodiments, oligonucleotides may be included in the PCR reactions. In other embodiments, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations" the disclosure of which is incorporated herein by reference in its entirety.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis)

developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., PNAS, USA, 89:7811-7815, 1992, the disclosure of which is incorporated herein by reference in its entirety.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D. C., Biotechnology Research, 11:1548-1552, 1993, the disclosure of which incorporated herein by reference in its entirety. Random and site-directed mutagenesis are described in Arnold, F. H., Current Opinion in Biotechnology, 4:450-455, 1993, the disclosure of which is incorporated herein by reference in its entirety.

In some embodiments, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis", and U.S. Pat. No. 5,939,250, filed May 22, 1996, entitled, "Production of Enzymes Having Desired Activities by Mutagenesis", both of which are incorporated herein by reference.

The variants of the polypeptides of Group B amino acid sequences may be variants in which one or more of the amino acid residues of the polypeptides of the Group B amino acid sequences are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue.

Other variants are those in which one or more of the amino acid residues of the polypeptides of the Group B amino acid sequences includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of Group B amino acid sequences, and sequences substantially identical thereto. In other embodiments, the fragment, derivative, or analog includes a proprotein, such that the fragment, derivative, or analog can be activated by cleavage of the proprotein portion to produce an active polypeptide.

Another aspect of the invention is polypeptides or fragments thereof which have at least about 50%, at least about 55%, at least about 60%, at least about 65%, at least about 70%, at least about 75%, at least about 80%, at least about 85%, at least about 90%, at least about 95%, or more than about 95% homology to one of the polypeptides of Group B amino acid sequences, and sequences substantially identical thereto, or a fragment comprising at least 5, 10, 15, 20, 25, 30, 35, 40, 50, 75, 100, or 150 consecutive amino acids thereof. Homology may be determined using any of the programs described above which aligns the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of Group B amino acid sequences, and sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of Group B amino acid sequences, and sequences substantially identical thereto, or a fragment comprising at least about 5, 10, 15, 20, 25, 30, 35, 40, 50, 75, 100, or 150 consecutive amino acids thereof using any of the programs described above.

Another aspect of the invention is an assay for identifying fragments or variants of Group B amino acid sequences, and sequences substantially identical thereto, which retain the enzymatic function of the polypeptides of Group B amino acid sequences, and sequences substantially identical thereto. For example the fragments or variants of said polypeptides, may be used to catalyze biochemical reactions, which indicate that the fragment or variant retains the enzymatic activity of the polypeptides in the Group B amino acid sequences.

The assay for determining if fragments of variants retain the enzymatic activity of the polypeptides of Group B amino acid sequences, and sequences substantially identical thereto includes the steps of: contacting the polypeptide fragment or variant with a substrate molecule under conditions which allow the polypeptide fragment or variant to function, and detecting either a decrease in the level of substrate or an increase in the level of the specific reaction product of the reaction between the polypeptide and substrate.

The polypeptides of Group B amino acid sequences, and sequences substantially identical thereto or fragments comprising at least 5, 10, 15, 20, 25, 30, 35, 40, 50, 75, 100, or 150 consecutive amino acids thereof may be used in a variety of applications. For example, the polypeptides or fragments thereof may be used to catalyze biochemical reactions. In accordance with one aspect of the invention, there is provided a process for utilizing the polypeptides of Group B amino acid sequences, and sequences substantially identical thereto or polynucleotides encoding such polypeptides for hydrolyzing glycosidic linkages. In such procedures, a substance containing a glycosidic linkage (e.g., a starch) is contacted with one of the polypeptides of Group B amino acid sequences, or sequences substantially identical thereto under conditions which facilitate the hydrolysis of the glycosidic linkage.

The polypeptides of Group B amino acid sequences, and sequences substantially identical thereto or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides of Group B amino acid sequences, and sequences substantially identical thereto, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of Group B amino acid sequences, and sequences substantially identical thereto, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 256:495-497, 1975, the disclosure of which is incorporated herein by reference), the trioma technique, the human B-cell hybridoma technique (Kozbor et al., Immunology Today 4:72, 1983, the disclosure of which is incorporated herein by reference), and the EBV-hybridoma technique (Cole, et al., 1985, in Monoclonal Antibodies and Cancer Therapy, Alan R. Liss, Inc., pp. 77-96, the disclosure of which is incorporated herein by reference).

Techniques described for the production of single chain antibodies (U.S. Pat. No. 4,946,778, the disclosure of which is incorporated herein by reference) can be adapted to produce single chain antibodies to the polypeptides of Group B amino acid sequences, and sequences substantially identical thereto, or fragments comprising at least 5, 10, 15, 20, 25, 30, 35, 40, 50, 75, 100, or 150 consecutive amino acids thereof Alternatively, transgenic mice may be used to express humanized antibodies to these polypeptides or fragments thereof.

Antibodies generated against the polypeptides of Group B amino acid sequences, and sequences substantially identical thereto, or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", *Methods in Enzymology*, Vol 160, pp. 87-116, which is hereby incorporated by reference in its entirety.

As used herein the term "nucleic acid sequence as set forth in SEQ ID Nos.: 23, 24, 25, 26, 27, 28, 29, 30, 31, and 32" encompasses the nucleotide sequences of Group A nucleic acid sequences, and sequences substantially identical thereto, as well as sequences homologous to Group A nucleic acid sequences, and fragments thereof and sequences complementary to all of the preceding sequences. The fragments include portions of SEQ ID Nos.: 23, 24, 25, 26, 27, 28, 29, 30, 31, and 32, comprising at least 10, 15, 20, 25, 30, 35, 40, 50, 75, 100, 150, 200, 300, 400, or 500 consecutive nucleotides of Group A nucleic acid sequences, and sequences substantially identical thereto. Homologous sequences and fragments of Group A nucleic acid sequences, and sequences substantially identical thereto, refer to a sequence having at least 99%, 98%, 97%, 96%, 95%, 90%, 85%, 80%, 75%, 70%, 65%, 60%, 55% or 50% homology to these sequences. Homology may be determined using any of the computer programs and parameters described herein, including FASTA version 3.0t78 with the default parameters. Homologous sequences also include RNA sequences in which uridines replace the thymines in the nucleic acid sequences as set forth in the Group A nucleic acid sequences. The homologous sequences may be obtained using any of the procedures described herein or may result from the correction of a sequencing error. It will be appreciated that the nucleic acid sequences as set forth in Group A nucleic acid sequences, and sequences substantially identical thereto, can be represented in the traditional single character format (See the inside back cover of Stryer, Lubert. *Biochemistry.* 3rd Ed. W. H Freeman & Co., New York.) or in any other format which records the identity of the nucleotides in a sequence.

As used herein the term "a polypeptide sequence as set forth in SEQ ID Nos: 33, 34, 35, 36, 37, 38, 39, 40, 41, and 42" encompasses the polypeptide sequence of Group B amino acid sequences, and sequences substantially identical thereto, which are encoded by a sequence as set forth in SEQ ID No.s: 33, 34, 35, 36, 37, 38, 39, 40, 41, and 42, polypeptide sequences homologous to the polypeptides of Group B amino acid sequences, and sequences substantially identical thereto, or fragments of any of the preceding sequences. Homologous polypeptide sequences refer to a polypeptide sequence having at least 99%, 98%, 97%, 96%, 95%, 90%, 85%, 80%, 75%, 70%, 65%, 60%, 55% or 50% homology to one of the polypeptide sequences of the Group B amino acid sequences. Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least 5, 10, 15, 20, 25, 30, 35, 40, 50, 75, 100, or 150 consecutive amino acids of the polypeptides of Group B amino acid sequences, and sequences substantially identical thereto. It will be appreciated that the polypeptide codes as set forth in Group B amino acid sequences, and sequences substantially identical thereto, can be represented in the traditional single character format or three letter format (See the inside back cover of Stryer, Lubert. Biochemistry 3rd Ed., W. H Freeman & Co., New York.) or in any other format which relates the identity of the polypeptides in a sequence.

It will be appreciated by those skilled in the art that a nucleic acid sequence as set forth in SEQ ID No.s: 23, 24, 25, 26, 27, 28, 29, 30, 31, and 32 and a polypeptide sequence as set forth in SEQ ID No.s: 33, 34, 35, 36, 37, 38, 39, 40, 41, and 42 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences as set forth in Group A nucleic acid sequences, and sequences substantially identical thereto, one or more of the polypeptide sequences as set forth in Group B amino acid sequences, and sequences substantially identical thereto. Another aspect of the invention is a computer readable medium having recorded thereon at least 2, 5, 10, 15, or 20 nucleic acid sequences as set forth in Group A nucleic acid sequences, and sequences substantially identical thereto.

Another aspect of the invention is a computer readable medium having recorded thereon one or more of the nucleic acid sequences as set forth in Group A nucleic acid sequences, and sequences substantially identical thereto. Another aspect of the invention is a computer readable medium having recorded thereon one or more of the polypeptide sequences as set forth in Group B amino acid sequences, and sequences substantially identical thereto. Another aspect of the invention is a computer readable medium having recorded thereon at least 2, 5, 10, 15, or 20 of the sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Embodiments of the invention include systems (e.g., internet based systems), particularly computer systems which store and manipulate the sequence information described herein. One example of a computer system 100 is illustrated in block diagram form in FIG. 1. As used herein, "a computer system" refers to the hardware components, software components, and data storage components used to analyze a nucleotide sequence of a nucleic acid sequence as set forth in Group A nucleic acid sequences, and sequences substantially identical thereto, or a polypeptide sequence as set forth in the Group B amino acid sequences. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of a nucleic acid sequence as set forth in Group A nucleic acid sequences, and sequences substantially identical thereto, or a polypeptide sequence as set forth in Group B amino acid sequences, and sequences substantially identical thereto, (such as search tools, compare tools, and modeling tools etc.) may reside in main memory 115 during execution.

In some embodiments, the computer system 100 may further comprise a sequence comparison algorithm for comparing a nucleic acid sequence as set forth in Group A nucleic acid sequences, and sequences substantially identical thereto, or a polypeptide sequence as set forth in Group B amino acid sequences, and sequences substantially identical thereto, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence as set forth in Group A nucleic acid sequences, and sequences substantially identical thereto, or a polypeptide sequence as set forth in Group B amino acid sequences, and sequences substantially identical thereto, stored on a computer readable medium to reference sequences stored on a computer readable medium to identify homologies or structural motifs. Various sequence comparison programs identified elsewhere in this patent specification are particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, http://weber.u.Washington.edu/~roach/human_genome_pro-gress 2.html) (Gibbs, 1995). At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) Mewes et al., 1997), and *D. melanogaster* (Adams et al., 2000). Significant progress has also been made in sequencing the genomes of model organism, such as mouse, *C. elegans*, and Arabadopsis sp. Several databases containing genomic information annotated with some functional information are maintained by different organization, and are accessible via the internet, for example, http://wwwtigr.org/tdb; http://www.genetics.wisc. edu; http ://genome-www-.stanford. edu/~ball; http://hiv-web.lanl.gov; http://www.ncbi.nlm.nih.gov; http://www.ebi.ac.uk; http://Pasteur.fr/other/biology; and http://www.genome.wi.mit.edu.

One example of a useful algorithm is BLAST and BLAST 2.0 algorithms, which are described in Altschul et al., Nuc. Acids Res. 25:3389-3402, 1977, and Altschul et al., J. Mol. Biol. 215:403-410, 1990, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value, the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, *Matrices for Detecting Distance Relationships: Atlas of Protein Sequence and Structure,* Washington: National Biomedical Research Foundation). BLAST programs are accessible through the U.S. National Library of Medicine, e.g., at www.ncbi.nlm.nih.gov.

The parameters used with the above algorithms may be adapted depending on the sequence length and degree of homology studied. In some embodiments, the parameters may be the default parameters used by the algorithms in the absence of instructions from the user.

Figure 2:
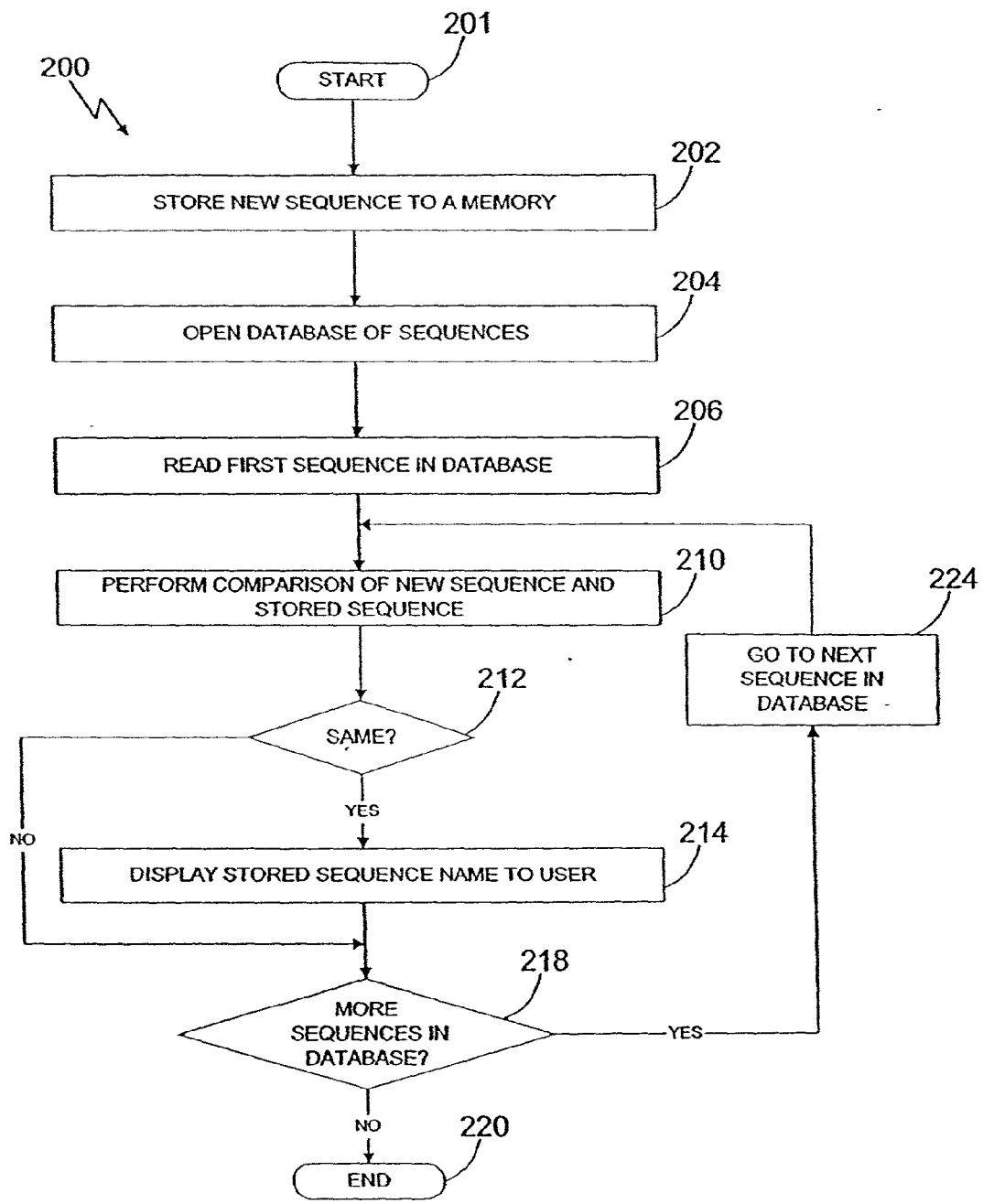
FIG. 2 is a flow diagram illustrating one embodiment of a process for comparing a new nucleotide or protein sequence with a database of sequences in order to determine the homology levels between the new sequence and the sequences in the database.

FIG. 2 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence as set forth in Group A nucleic acid sequences, and sequences substantially identical thereto, or a polypeptide sequence as set forth in Group B amino acid sequences, and sequences substantially identical thereto, a data storage device having retrievably stored thereon reference nucleotide sequences or polypeptide sequences to be compared to a nucleic acid sequence as set forth in Group A nucleic acid sequences, and sequences substantially identical thereto, or a polypeptide sequence as set forth in Group B amino acid sequences, and sequences substantially identical thereto, and a sequence comparer for conducting the comparison. The sequence comparer may indicate a homology level between the sequences compared or identify structural motifs in the above described nucleic acid code of Group A nucleic acid sequences, and sequences substantially identical thereto, or a polypeptide sequence as set forth in Group B amino acid sequences, and sequences substantially identical thereto, or it may identify structural motifs in sequences which are compared to these nucleic acid codes and polypeptide codes. In some embodiments, the data storage device may have stored thereon the sequences of at least 2, 5, 10, 15, 20, 25, 30 or 40 or more of the nucleic acid sequences as set forth in Group A nucleic acid sequences, and sequences substantially identical thereto, or the polypeptide sequences as set forth in Group B amino acid sequences, and sequences substantially identical thereto.

Another aspect of the invention is a method for determining the level of homology between a nucleic acid sequence as set forth in Group A nucleic acid sequences, and sequences substantially identical thereto, or a polypeptide sequence as set forth in Group B amino acid sequences, and sequences substantially identical thereto, and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, 30 or 40 or more of the above described nucleic acid sequences as set forth in the Group A nucleic acid sequences, or the polypeptide sequences as set forth in the Group B amino acid sequences through use of the computer program and determining homology between the nucleic acid codes or polypeptide codes and reference nucleotide sequences or polypeptide sequences.

Figure 3:
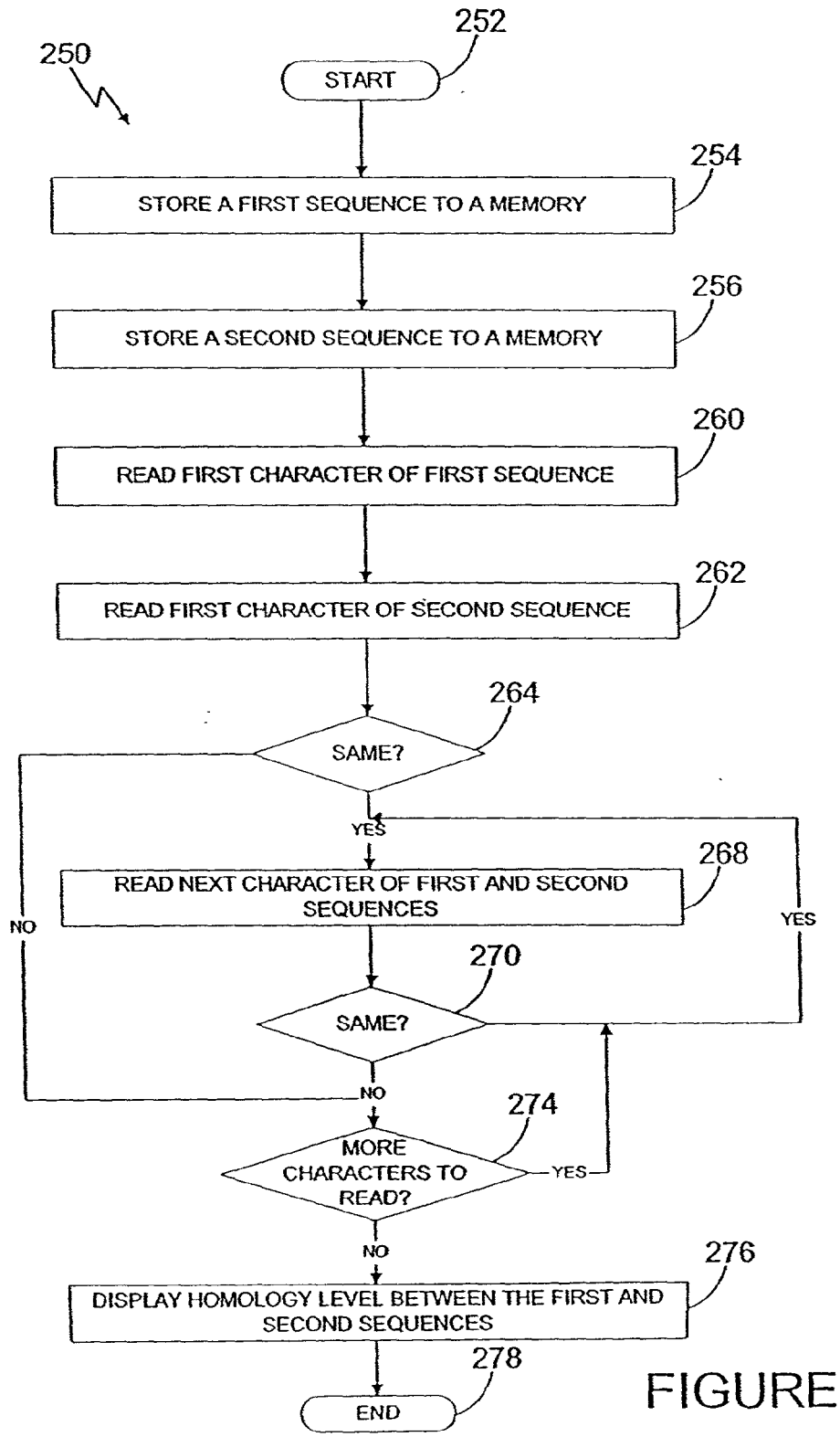
FIG. 3 is a flow diagram illustrating one embodiment of a process in a computer for determining whether two sequences are homologous.
Figure 4:
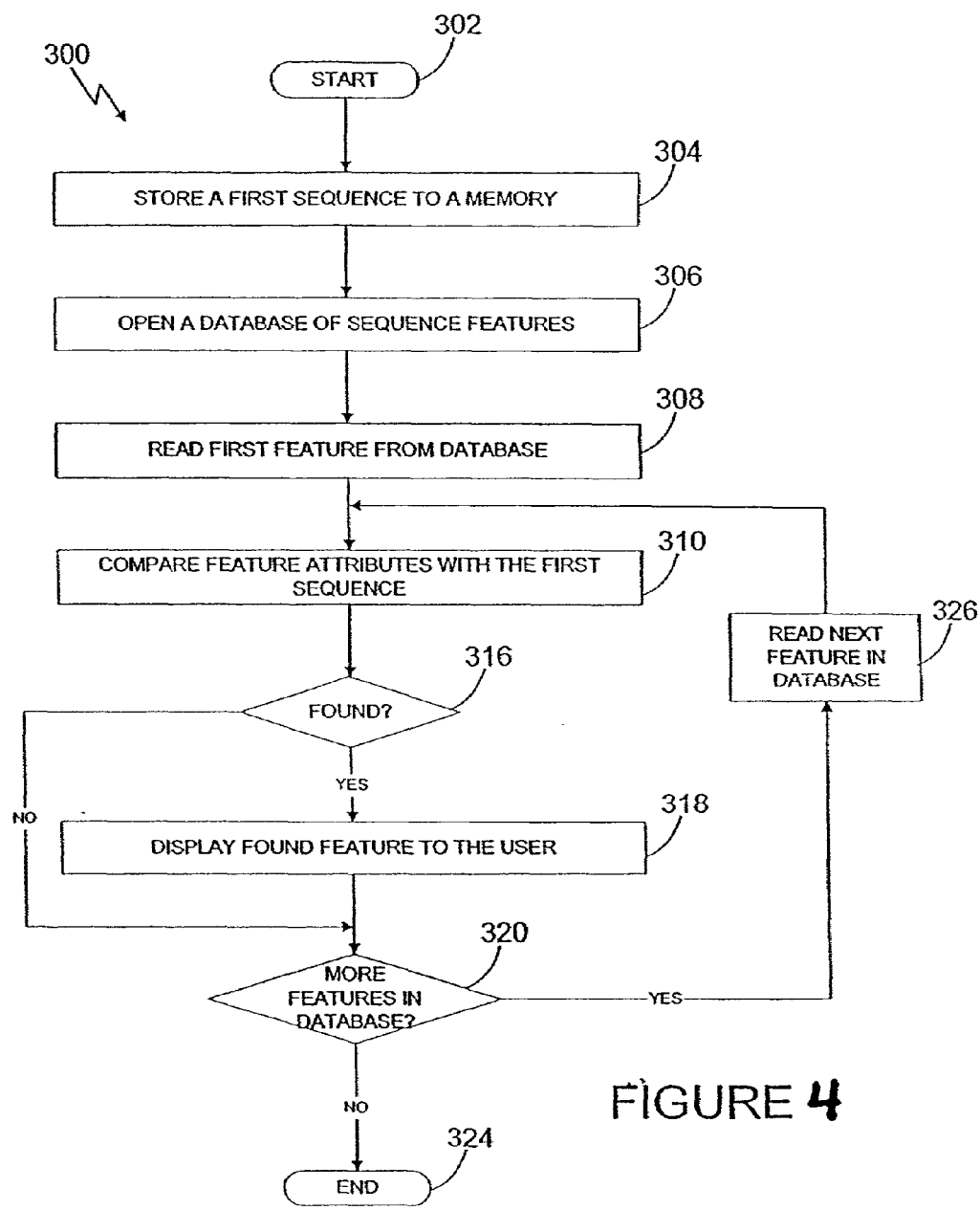
FIG. 4 is a flow diagram illustrating one embodiment of an identifier process 300 for detecting the presence of a feature in a sequence.

FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of Group A nucleic acid sequences, and sequences substantially identical thereto, differs from a reference nucleic acid sequence at one or more positions. Optionally such a program records the length and identity of inserted, deleted or substituted nucleotides with respect to the sequence of either the reference polynucleotide or a nucleic acid sequence as set forth in Group A nucleic acid sequences, and sequences substantially identical thereto. In one embodiment, the computer program may be a program which determines whether a nucleic acid sequence as set forth in Group A nucleic acid sequences, and sequences substantially identical thereto, contains a single nucleotide polymorphism (SNP) with respect to a reference nucleotide sequence.

Accordingly, another aspect of the invention is a method for determining whether a nucleic acid sequence as set forth in Group A nucleic acid sequences, and sequences substantially identical thereto, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 3. The method may also be performed by reading at least 2, 5, 10, 15, 20, 25, 30, or 40 or more of the nucleic acid sequences as set forth in Group A nucleic acid sequences, and sequences substantially identical thereto, and the reference nucleotide sequences through the use of the computer program and identifying differences between the nucleic acid codes and the reference nucleotide sequences with the computer program.

In other embodiments the computer based system may further comprise an identifier for identifying features within a nucleic acid sequence as set forth in the Group A nucleic acid sequences or a polypeptide sequence as set forth in Group B amino acid sequences, and sequences substantially identical thereto.

An "identifier" refers to one or more programs which identifies certain features within a nucleic acid sequence as set forth in Group A nucleic acid sequences, and sequences substantially identical thereto, or a polypeptide sequence as set forth in Group B amino acid sequences, and sequences substantially identical thereto. In one embodiment, the identifier may comprise a program which identifies an open reading frame in a nucleic acid sequence as set forth in Group A nucleic acid sequences, and sequences substantially identical thereto.

FIG. 5 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (www.gcg.com). Alternatively, the features may be structural polypeptide motifs such as alpha helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence as set forth in Group A nucleic acid sequences, and sequences substantially identical thereto, or a polypeptide sequence as set forth in Group B amino acid sequences, and sequences substantially identical thereto, comprising reading the nucleic acid code(s) or polypeptide code(s) through the use of a computer program which identifies features therein and identifying features within the nucleic acid code(s) with the computer program. In one embodiment, computer program comprises a computer program which identifies open reading frames. The method may be performed by reading a single sequence or at least 2, 5, 10, 15, 20, 25, 30, or 40 of the nucleic acid sequences as set forth in Group A nucleic acid sequences, and sequences substantially identical thereto, or the polypeptide sequences as set forth in Group B amino acid sequences, and sequences substantially identical thereto, through the use of the computer program and identifying features within the nucleic acid codes or polypeptide codes with the computer program.

A nucleic acid sequence as set forth in Group A nucleic acid sequences, and sequences substantially identical thereto, or a polypeptide sequence as set forth in Group B amino acid sequences, and sequences substantially identical thereto, may be stored and manipulated in a variety of data processor programs in a variety of formats. For example, a nucleic acid sequence as set forth in Group A nucleic acid sequences, and sequences substantially identical thereto, or a polypeptide sequence as set forth in Group B amino acid sequences, and sequences substantially identical thereto, may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence as set forth in Group A nucleic acid sequences, and sequences substantially identical thereto, or a polypeptide sequence as set forth in Group B amino acid sequences, and sequences substantially identical thereto. The following list is intended not to limit the invention but to provide guidance to programs and databases which are useful with the nucleic acid sequences as set forth in Group A nucleic acid sequences, and sequences substantially identical thereto, or the polypeptide sequences as set forth in Group B amino acid sequences, and sequences substantially identical thereto.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds, such as small molecules. Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original small molecule or compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods.

In a particular embodiment, the invention provides a method for modifying small molecules, comprising contacting a polypeptide encoded by a polynucleotide described herein or enzymatically active fragments thereof with a small molecule to produce a modified small molecule. A library of modified small molecules is tested to determine if a modified small molecule is present within the library which exhibits a desired activity. A specific biocatalytic reaction which produces the modified small molecule of desired activity is identified by systematically eliminating each of the biocatalytic reactions used to produce a portion of the library, and then testing the small molecules produced in the portion of the library for the presence or absence of the modified small molecule with the desired activity. The specific biocatalytic reactions which produce the modified small molecule of desired activity is optionally repeated. The biocatalytic reactions are conducted with a group of biocatalysts that react with distinct structural moieties found within the structure of a small molecule, each biocatalyst is specific for one structural moiety or a group of related structural moieties; and each biocatalyst reacts with many different small molecules which contain the distinct structural moiety.

The invention will be further described with reference to the following examples; however, it is to be understood that the invention is not limited to such examples.

EXAMPLES

Example 1

Bacterial Expression and Purification of Esterases

DNA encoding the enzymes of the present invention, SEQ ID NOS:33 through 42, were initially amplified from a pBluescript vector containing the DNA by the PCR technique using the primers noted herein. The amplified sequences were then inserted into the respective PQE vector listed beneath the primer sequences, and the enzyme was expressed according to the protocols set forth herein. The 5' and 3' primer sequences for the respective genes are as follows:

```
Straphylothermus marinus F1-12LC

5' CCGAGAATTC ATTAAAGAGG AGAAATTAAC TATGTCTTTA AACAAGCACT CT
    3' CGGAAGATCT CTATCGTTTA GTGTATGATT T
    vector: pQET Pyrodictium TAG11-17LC 5' CCGAGAATTC ATTAAAGAGG AGAAATTAAC TATGAAACTC CTTGAGCCCA
    CA EcoR1
    3' CGGAAGATCT CGCCGGTACA CCATCAGCCA C BglII
    vector: pQET Archaeoglobus venificus SNP6-24LC 5' CCGAGAATTC ATTAAAGAGG AGAAATTAAC TATGCCATAT GTTAGGAATG
    GT
    3' CGGAGGTACC TTAGAACTGT GCTGAAGAAA TAAATTCGTC CATTGCTCT
    3' CGGAGGTACC TTAGAACTGT GCTGAAGAAA TAAATTCGTC CATTGCTCTA
    TTA vector: pQET Aquifex pyrophilus - 28LC 5' CCGAGAATTC ATTAAAGAGG AGAAATTAAC TATGAGATTG AGGAAATTTG
    AAG
    3' CGGAGGTACC CTATTCAGAA AGTACCTCTA A
    vector: pQET

M11TL - 29LC

5' CCGAGAATTC ATTAAAGAGG AGAAATTAAC TATGTTTAAT ATCAATGTCT TT
    3' CGGAAGATCT TTAAGGATTT TCCCTGGGTA G
    vector: pQET
```

-continued

Thermococcus CL-2 - 30LC

```
5' CCGAGAATTC ATTAAAGAGG AGAAATTAAC TATGGAGGTT TACAAGGCCA
AA
3' CGGAGGTACC TTATTGAGCC GAAGAGTACG A
vector: pQET
```

Aquifex VF5 - 34LC

```
5' CCGAGAATTC ATTAAAGAGG AGAAATTAAC TATGATTGGC AATTTGAAAT
TGA EcoRI
3' CGGAGGTACC TTAAAGTGCT CTCATATCCC C KpnI
vector: pQET
```

Teredinibacter 42L

```
5' CCGAGAATTC ATTAAAGAGG AGAAATTAAC TATGCCAGCT AATGACTCAC
CC
3' CGGAAGATCT TCAACAGGCT CCAAATAATT TC (without His-tag)
3' CGGAAGATCT ACAGGCTCCA AATAATTTC (with His-tag)
vector: pQE12
```

Archaeoglobus fulgidus VC16-16MC

```
5' CCGAGAATTC ATTAAAGAGG AGAAATTAAC TATGCTTGAT ATGCCAATCG
AC EcoR1
3'CGGAGGTACC CTAGTCGAAG ACAAGAAGAG C Kpnl
vector: pQET
```

Sulfolabus solfataricus P1-8LC

```
5' CCGAGAATTC ATTAAAGAGG AGAAATTAAC TATGCCCCAG GATCCTAGAA
TT EcoR1
3' CGGAGGTACC TTAAATTTTA TCATAAAATA C Kpnl
vector: pQET
```

The restriction enzyme sites indicated correspond to the restriction enzyme sites on the bacterial expression vector indicated for the respective gene (Qiagen, Inc. Chatsworth, Calif.). The pQE vector encodes antibiotic resistance (Amp[1]), a bacterial origin of replication (ori), an IPTG-regulatable promoter operator (P/O), a ribosome binding site (RBS), a 6His tag and restriction enzyme sites.

The pQE vector was digested with the restriction enzymes indicated. The amplified sequences were ligated into the respective pQE vector and inserted in frame with the sequence encoding for the RBS. The ligation mixture was then used to transform the E. coli strain M15/pREP4 (Qiagen, Inc.) by electroporation. M15/pREP4 contains multiple copies of the plasmid pREP4, which expresses the lacI repressor and also confers kanamycin resistance (Kan[1]). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 µg/ml) and Kan (25 µg/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lad repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

Example 2

Isolation of a Selected Clone from the Deposited Genomic Clones

The two oligonucleotide primers corresponding to the gene of interest are used to amplify the gene from the deposited material. A polymerase chain reaction is carried out in 25 µl of reaction mixture with 0.1 µg of the DNA of the gene of interest. The reaction mixture is 1.5-5 mM MgCl2, 0.01% (w/v) gelatin, 20 µM each of dATP, dCTP, dGTP, dTTP, 25 pmol of each primer and 1.25 Unit of Taq polymerase. Thirty cycles of PCR (denaturation at 94° C. for 1 min; annealing at 55° C. for 1 min; elongation at 72° C. for 1 min) are performed with the Perkin-Elmer Cetus 9600 thermal cycler. The amplified product is analyzed by agarose gel electrophoresis and the DNA band with expected molecular weight is excised and purified. The PCR product is verified to be the gene of interest by subcloning and sequencing the DNA product.

Example 3

Production of the Expression Gene Bank

Colonies containing pBluescript plasmids with random inserts from the organisms M11TL, Thermococcus GU5L5, and Teredinibacter were obtained according to the method of Hay and Short, Strategies, 5:16, 1992.

Example 4

Screening for Lipase/Esterase Activity

The resulting colonies were picked with sterile toothpicks and used to singly inoculate each of the wells of 96-well microtiter plates. The wells contained 250 μL of LB media with 100 μg/mL ampicillin, 80 μg/mL methicillin, and 10% v/v glycerol (LB Amp/Meth, glycerol). The cells were grown overnight at 370° C. without shaking. This constituted generation of the "Source GeneBank." Each well of the Source GeneBank thus contained a stock culture of E. coli cells, each of which contained a pBluescript with a unique DNA insert.

The plates of the Source GeneBank were used to multiply inoculate a single plate (the "Condensed Plate") containing in each well 200 μL of LB Amp/Meth, glycerol. This step was performed using the High Density Replicating Tool (HDRT) of the Beckman Biomek with a 1% bleach, water, isopropanol, air-dry sterilization cycle in between each inoculation. Each well of the Condensed Plate thus contained 10 to 12 different pBluescript clones from each of the source library plates. The Condensed Plate was grown for 16 hours at 37° C. and then used to inoculate two white 96-well Polyfiltronics microtiter daughter plates containing in each well 250 ||L of LB Amp/Meth (no glycerol). The original condensed plate was put in storage –80° C. The two condensed daughter plates were incubated at 37° C. for 18 hours.

The short chain esterase '600 μM substrate stock solution' was prepared as follows: 25 mg of each of the following compounds was dissolved in the appropriate volume of DMSO to yield a 25.2 mM solution. The compounds used were 4-methylumbelliferyl proprionoate, 4-methylumbelliferyl butyrate, and 4-methylumbelliferyl heptanoate. Two hundred fifty microliters of each DMSO solution was added to ca 9 mL of 50 mM, pH 7.5 Hepes buffer which contained 0.6% of Triton X-100 and 0.6 mg per mL of dodecyl maltoside (Anatrace). The volume was taken to 10.5 mL with the above Hepes buffer to yield a slightly cloudy suspension.

The long chain '600 μM substrate stock solution' was prepared as follows: 25 mg of each of the following compounds was dissolved in DMSO to 25.2 mM as above. The compounds used were 4-methylumbelliferyl elaidate, 4-methylumbelliferyl palmitate, 4-methylumbelliferyl oleate, and 4-methylumbelliferyl stearate. All required brief warming in a 70° C. bath to achieve dissolution. Two hundred fifty microliters of each DMSO solution was added to the Hepes buffer and diluted to 10.5 mL as above. All seven umbelliferones were obtained from Sigma Chemical Co.

Fifty μL of the long chain esterase or short chain esterase '600 M substrate stock solution' was added to each of the wells of a white condensed plate using the Biomek to yield a final concentration of substrate of about 100 μM. The fluorescence values were recorded (excitation=326 nm, emission=450 nm) on a plate-reading fluorometer immediately after addition of the substrate. The plate was incubated at 70° C. for 60 minutes in the case of the long chain substrates, and 30 minutes at RT in the case of the short chain substrates. The fluorescence values were recorded again. The initial and final fluorescence values were compared to determine if an active clone was present.

Example 5

Isolation and Purification of the Active Clone

To isolate the individual clone which carried the activity, the Source GeneBank plates were thawed and the individual wells used to singly inoculate a new plate containing LB Amp/Meth. As above, the plate was incubated at 37° C. to grow the cells, 50 μL of 600 μM substrate stock solution was added using the Biomek and the fluorescence was determined Once the active well from the source plate was identified, cells from this active well were streaked on agar with LB/Amp/Meth and grown overnight at 37° C. to obtain single colonies. Eight single colonies were picked with a sterile toothpick and used to singly inoculate the wells of a 96-well microtiter plate. The wells contained 250 μL of LB Amp/Meth. The cells were grown overnight at 37° C. without shaking. A 200 μL aliquot was removed from each well and assayed with the appropriate long or short chain substrates as above. The most active clone was identified and the remaining 50 μL of culture was used to streak an agar plate with LB/Amp/Meth. Eight single colonies were picked, grown and assayed as above. The most active clone was used to inoculate 3 mL cultures of LB/Amp/Meth, which were grown overnight. The plasmid DNA was isolated from the cultures and utilized for sequencing.

While the invention has been described in detail with reference to certain preferred embodiments thereof, it will be understood that modifications and variations are within the sprit and scope of that which is described and claimed.

What is claimed is:

1. An isolated, synthetic or recombinant nucleic acid comprising (a) a sequence having at least 95% sequence identity to SEQ ID NO:26, and encoding a polypeptide having an esterase activity, or, (b) a sequence completely complementary to (a) wherein said esterase activity comprises the hydrolysis of at least one ester selected from the group consisting of 4-methylumbelliferyl proprionate, 4-methylumbelliferyl butyrate, 4-methylumbelliferyl heptanoate, 4-methylumbelliferyl elaidate, 4-methylumbelliferyl palmitate, 4-methylumbelliferyl oleate, and 4-methylumbelliferyl stearate.

2. An isolated, synthetic or recombinant nucleic acid of claim 1, comprising a sequence comprising SEQ ID NO:26 or sequences completely complementary thereto.

3. An isolated, synthetic or recombinant nucleic acid (a) encoding a polypeptide having an esterase activity comprising a sequence that hybridizes to the nucleic acid of SEQ ID NO:26 or (b) sequences completely complementary to (a),
   wherein the hybridization conditions comprise a wash for 30 minutes at room temperature in 150 mM NaCl, 20 mM Tris hydrochloride, pH 7.8, 1 mM Na$_2$EDTA containing 0.5% SDS, followed by a 30 minute wash in fresh 1× SET at T$_m$–10 C. wherein said esterase activity comprises the hydrolysis of at least one ester selected from the group consisting of 4-methylumbelliferyl proprionate, 4-methylumbelliferyl butyrate, 4-methylumbelliferyl heptanoate, 4-methylumbelliferyl elaidate, 4-methylumbelliferyl palmitate, 4-methylumbelliferyl oleate, and 4-methylumbelliferyl stearate.

4. The isolated, synthetic or recombinant nucleic acid of claim 1, wherein the sequence identity to SEQ ID NO:26 is at least 97%.

5. An isolated, synthetic or recombinant nucleic acid comprising a sequence (i) encoding (a) a polypeptide having an esterase activity and having at least 95% sequence identity to the sequence of SEQ ID NO:36, or, (b) enzymatically active fragments of (a); or (ii) fully complementary to (i) wherein said esterase activity comprises the hydrolysis of at least one ester selected from the group consisting of 4-methylumbelliferyl proprionate, 4-methylumbelliferyl butyrate, 4-methylumbelliferyl heptanoate, 4-methylumbelliferyl elaidate, 4-methylumbelliferyl palmitate, 4-methylumbelliferyl oleate, and 4-methylumbelliferyl stearate.

6. A method of producing a polypeptide having an esterase activity comprising introducing a nucleic acid as set forth in claim 1 into a host cell under conditions that allow expression of the nucleic acid to produce a polypeptide.

7. A nucleic acid probe for isolation or identification of esterase genes comprising an oligonucleotide having the nucleic acid sequence of claim 3 or (b) a sequence completely complementary to (a).

8. The probe of claim 7, wherein the oligonucleotide comprises DNA or RNA.

9. The probe of claim 7, wherein the probe further comprises a detectable isotopic label.

10. The probe of claim 7, wherein the probe further comprises a detectable non-isotopic label selected from the group consisting of a fluorescent molecule, a chemiluminescent molecule, an enzyme, a cofactor, an enzyme substrate, and a hapten.

11. A vector comprising a nucleic acid as set forth in claim 1.

12. The vector of claim 11, wherein the vector comprises a viral particle, a baculovirus, a phage, a plasmid, a cosmid, a fosmid, a bacterial artificial chromosome, a viral DNA or a P1-based artificial chromosome.

13. A isolated host cell comprising a nucleic acid as set forth in claim 1.

14. The isolated host cell of claim 13 comprising a eukaryotic cell or a prokaryotic cell.

15. The isolated host cell of claim 14 comprising a plant cell, a mammalian cell, a fungal cell, a bacterial cell, a yeast cell or an insect cell.

16. The isolated, synthetic or recombinant nucleic acid of claim 1 (a), wherein the esterase activity comprises catalyzing the hydrolysis of said ester to an organic acid and an alcohol.

17. The isolated, synthetic or recombinant nucleic acid of claim 3 (a), wherein the esterase activity comprises catalyzing the hydrolysis of said ester to an organic acid and an alcohol.

18. The isolated, synthetic or recombinant nucleic acid of claim 4, wherein the sequence identity to SEQ ID NO:26 is at least 98%.

19. A vector comprising a nucleic acid as set forth in claim 3.

20. The vector of claim 19, wherein the vector comprises a viral particle, a baculovirus, a phage, a plasmid, a cosmid, a fosmid, a bacterial artificial chromosome, a viral DNA or a P1-based artificial chromosome.

21. A isolated host cell comprising a nucleic acid as set forth in claim 3.

22. The isolated host cell of claim 21, wherein the cell is a eukaryotic cell or a prokaryotic cell.

23. The isolated host cell of claim 21, wherein the cell is a plant cell, a mammalian cell, a fungal cell, a bacterial cell, a yeast cell or an insect cell.

* * * * *

SEQUENCE LISTING

```
<160> NUMBER OF SEQ ID NOS: 42

<210> SEQ ID NO 1
<211> LENGTH: 52
<212> TYPE: DNA
<213> ORGANISM: Artificial sequence
<220> FEATURE:
<223> OTHER INFORMATION: Primer for PCR

<400> SEQUENCE: 1
ccgagaattc attaaagagg agaaattaac tatgtcttta aacaagcact ct              52

<210> SEQ ID NO 2
<211> LENGTH: 31
<212> TYPE: DNA
<213> ORGANISM: Artificial sequence
<220> FEATURE:
```

```
<223> OTHER INFORMATION: Primer for PCR

<400> SEQUENCE: 2
tttagtatgt gatttgctat ctctagaagg c                                    31

<210> SEQ ID NO 3
<211> LENGTH: 52
<212> TYPE: DNA
<213> ORGANISM: Artificial sequence
<220> FEATURE:
<223> OTHER INFORMATION: Primer for PCR

<400> SEQUENCE: 3
ccgagaattc attaaagagg agaaattaac tatgaaactc cttgagccca ca             52

<210> SEQ ID NO 4
<211> LENGTH: 31
<212> TYPE: DNA
<213> ORGANISM: Artificial sequence
<220> FEATURE:
<223> OTHER INFORMATION: Primer for PCR

<400> SEQUENCE: 4
caccgactac cacatggccg ctctagaagg c                                    31

<210> SEQ ID NO 5
<211> LENGTH: 52
<212> TYPE: DNA
<213> ORGANISM: Artificial sequence
<220> FEATURE:
<223> OTHER INFORMATION: Primer for PCR

<400> SEQUENCE: 5
ccgagaattc attaaagagg agaaattaac tatgccatat gttaggaatg gt             52

<210> SEQ ID NO 6
<211> LENGTH: 49
<212> TYPE: DNA
<213> ORGANISM: Artificial sequence
<220> FEATURE:
<223> OTHER INFORMATION: Primer for PCR

<400> SEQUENCE: 6
tctcgttacc tgcttaaata aagaagtcgt gtcaagattc catggaggc                 49

<210> SEQ ID NO 7
<211> LENGTH: 50
<212> TYPE: DNA
<213> ORGANISM: Artificial sequence
<220> FEATURE:
<223> OTHER INFORMATION: Primer for PCR

<400> SEQUENCE: 7
atctcgttac ctgcttaaat aaagaagtcg tgtcaagatt ccatggaggc                50

<210> SEQ ID NO 8
<211> LENGTH: 53
<212> TYPE: DNA
<213> ORGANISM: Artificial sequence
<220> FEATURE:
<223> OTHER INFORMATION: Primer for PCR

<400> SEQUENCE: 8
ccgagaattc attaaagagg agaaattaac tatgagattg aggaaatttg aag            53
```

<210> SEQ ID NO 9
<211> LENGTH: 31
<212> TYPE: DNA
<213> ORGANISM: Artificial sequence
<220> FEATURE:
<223> OTHER INFORMATION: Primer for PCR

<400> SEQUENCE: 9
aatctccatg aaagacttat cccatggagg c                          31

<210> SEQ ID NO 10
<211> LENGTH: 52
<212> TYPE: DNA
<213> ORGANISM: Artificial sequence
<220> FEATURE:
<223> OTHER INFORMATION: Primer for PCR

<400> SEQUENCE: 10
ccgagaattc attaaagagg agaaattaac tatgtttaat atcaatgtct tt    52

<210> SEQ ID NO 11
<211> LENGTH: 31
<212> TYPE: DNA
<213> ORGANISM: Artificial sequence
<220> FEATURE:
<223> OTHER INFORMATION: Primer for PCR

<400> SEQUENCE: 11
gatgggtccc ttttaggaat ttctagaagg c                          31

<210> SEQ ID NO 12
<211> LENGTH: 52
<212> TYPE: DNA
<213> ORGANISM: Artificial sequence
<220> FEATURE:
<223> OTHER INFORMATION: Primer for PCR

<400> SEQUENCE: 12
ccgagaattc attaaagagg agaaattaac tatggaggtt tacaaggcca aa    52

<210> SEQ ID NO 13
<211> LENGTH: 31
<212> TYPE: DNA
<213> ORGANISM: Artificial sequence
<220> FEATURE:
<223> OTHER INFORMATION: Primer for PCR

<400> SEQUENCE: 13
agcatgagaa gccgagttat tccatggagg c                          31

<210> SEQ ID NO 14
<211> LENGTH: 53
<212> TYPE: DNA
<213> ORGANISM: Artificial sequence
<220> FEATURE:
<223> OTHER INFORMATION: Primer for PCR

<400> SEQUENCE: 14
ccgagaattc attaaagagg agaaattaac tatgattggc aatttgaaat tga   53

<210> SEQ ID NO 15
<211> LENGTH: 31
<212> TYPE: DNA
<213> ORGANISM: Artificial sequence
<220> FEATURE:
<223> OTHER INFORMATION: Primer for PCR -continued

```
<400> SEQUENCE: 15
cccctatact ctcgtgaaat tccatggagg c                                    31

<210> SEQ ID NO 16
<211> LENGTH: 52
<212> TYPE: DNA
<213> ORGANISM: Artificial sequence
<220> FEATURE:
<223> OTHER INFORMATION: Primer for PCR

<400> SEQUENCE: 16
ccgagaattc attaaagagg agaaattaac tatgccagct aatgactcac cc              52

<210> SEQ ID NO 17
<211> LENGTH: 32
<212> TYPE: DNA
<213> ORGANISM: Artificial sequence
<220> FEATURE:
<223> OTHER INFORMATION: Primer for PCR

<400> SEQUENCE: 17
ctttaataaa cctcggacaa cttctagaag gc                                   32

<210> SEQ ID NO 18
<211> LENGTH: 29
<212> TYPE: DNA
<213> ORGANISM: Artificial sequence
<220> FEATURE:
<223> OTHER INFORMATION: Primer for PCR

<400> SEQUENCE: 18
ctttaataaa cctcggacat ctagaaggc                                       29

<210> SEQ ID NO 19
<211> LENGTH: 52
<212> TYPE: DNA
<213> ORGANISM: Artificial sequence
<220> FEATURE:
<223> OTHER INFORMATION: Primer for PCR

<400> SEQUENCE: 19
ccgagaattc attaaagagg agaaattaac tatgcttgat atgccaatcg ac              52

<210> SEQ ID NO 20
<211> LENGTH: 31
<212> TYPE: DNA
<213> ORGANISM: Artificial sequence
<220> FEATURE:
<223> OTHER INFORMATION: Primer for PCR

<400> SEQUENCE: 20
cgagaagaac agaagctgat cccatggagg c                                    31

<210> SEQ ID NO 21
<211> LENGTH: 52
<212> TYPE: DNA
<213> ORGANISM: Artificial sequence
<220> FEATURE:
<223> OTHER INFORMATION: Primer for PCR

<400> SEQUENCE: 21
ccgagaattc attaaagagg agaaattaac tatgcccta gatcctagaa tt               52

<210> SEQ ID NO 22
<211> LENGTH: 31
```

<212> TYPE: DNA
<213> ORGANISM: Artificial sequence
<220> FEATURE:
<223> OTHER INFORMATION: Primer for PCR

<400> SEQUENCE: 22
cataaaatac tattttaaat tccatggagg c                                31

<210> SEQ ID NO 23
<211> LENGTH: 555
<212> TYPE: DNA
<213> ORGANISM: Staphylothermus Marinus

<400> SEQUENCE: 23
atgtctttaa acaagcactc ttggatggat atgataatat ttattctcag cttttctttc    60
ccattaacaa tgatcgcatt agctatctct atgtcgtcat ggtttaatat atggaataat   120
gcattaagcg atctaggaca tgctgttaaa agcagtgttg ctccaatatt caatctaggt   180
cttgcaattg gtgggatact aattgttata gttggtttaa gaaatctttta ttcgtggagt   240
agagttaaag gatctttaat catatccatg ggtgtatttc ttaacttaat agggttttc    300
gacgaagtat atggttggat acatttccta gtctcagtat tgttttctt atcaataata    360
gcatatttca tagctatatc aatacttgac aaatcatgga tagctgttct actaataata   420
ggtcatattg caatgtggta tctacacttt gcttcagaga ttccgagagg tgcggctatt   480
cccgagttat tagcggtatt ctcgttttta ccattctata agagacta ttttaaatca     540
tacactaaac gatag                                                    555

<210> SEQ ID NO 24
<211> LENGTH: 1041
<212> TYPE: DNA
<213> ORGANISM: Pyrodictium

<400> SEQUENCE: 24
atgaaactcc ttgagcccac aaatacctcc tacacgctgt tacaggattt agcattgcat    60
tttgcatttt actggtttct ggccgtgtat acgtggttac ccgtgtcct agtccggggc    120
gtagctgtgg acacaggggt ggctcgggtg cctgggctcg gccggcgcgg taagaggctg   180
ctcctggccg ctgtgctgt cttggcgctt ttgtgtccg ttgttgtccc ggcttatgtg     240
gcgtatagta gtctgcaccc ggagagctgt cggcccgttg cgccggaggg gctcacctac   300
aaagagttca gcgtgaccgc ggaggatggc ttggtggttc ggggctgggt gctgggcccc   360
ggcgctgggg gcaacccggt gttcgttttg atgcacgggt atactgggtg ccgctcggcg   420
ccctacatgg ctgtgctggc ccgggagctc gtggagtggg ggtacccggt ggttgtgttc   480
gacttccggg gccacgggga gagcgggggc tcgacgacga ttgggccccg ggaggtgctg   540
gatgcccggg ctgtggtggg ctatgtctcg gagcggttcc ccggccgccg gataatattg   600
gtggggttca gtatgggcgg cgctgtagcg atcgtggagg gtgctgggga cccgcgggtc   660
tacgcggtgg ctgctgatag cccgtactat aggctccggg acgtcatacc ccggtggctg   720
gagtacaaga cgccgctgcc gggctgggtg ggtgtgctgg ccgggttcta cgggaggctg   780
atggcgggcg ttgacctcgg cttcggcccc gctggggtgg agcgcgtgga taagccgttg   840
ctggtggtgt atgggccccg ggaccccgctg gtgacgcggg acgaggcgag gagcctggcg   900
tcccgtagcc cgtgtggccg tctcgtcgag gttcctgggg ctggccacgt ggaggccgtg   960
gatgtgctcg ggccgggccg ctacgcagac atgctgatag agctggcgca cgaggagtgc  1020

-continued

| cctccggggg ccggtggctg a | 1041 |

<210> SEQ ID NO 25
<211> LENGTH: 789
<212> TYPE: DNA
<213> ORGANISM: Archaeoglobus veneficus

<400> SEQUENCE: 25

| atgccatatg ttaggaatgg tgtgtaaat atctattatg aactggtgga tggacctgag | 60 |
| ccaccaattg tctttgttca cggatggaca gcaaatatga attttggaa agagcaaaga | 120 |
| cgttattttg caggcaggaa tatgatgttg tttgtcgata acagaggtca tggcaggtcc | 180 |
| gataagccac ttggatacga tttctacaga tttgagaact tcatttcaga tttagatgcg | 240 |
| gttgttaggg agactggagt ggagaaattt gttctcgtcg acattccatt cggaacaatg | 300 |
| atctctatga agtactgttc ggagtatcgg aatcgggttc ttgctctaat cctcataggt | 360 |
| ggtgggagca aataaagct tctacacaga attggatatc ctttagcaaa gattcttgca | 420 |
| tccattgcat acaagaagtc ttcaagattg gtcgcagatc tttcctttgg caaaaatgct | 480 |
| ggtgaactta agagtggggg atggaaacag gcaatggatt atacaccctc ctacgtggca | 540 |
| atgtacacgt acagaactct aacgaaagtg aatcttgaaa atatcttgga gaaaatagac | 600 |
| tgtccaacac tgattatcgt tggagaagag gatgcactat tgcccgttag caaatcagtt | 660 |
| gagctgagca ggaggataga aaactcaaag cttgtgatca tcccaaactc ggggcattgc | 720 |
| gtaatgcttg agagtccaag tgaggttaat agagcaatgg acgaattcat ttcttcagca | 780 |
| cagttctaa | 789 |

<210> SEQ ID NO 26
<211> LENGTH: 756
<212> TYPE: DNA
<213> ORGANISM: Aquifex pyrophilus

<400> SEQUENCE: 26

| ttgagattga ggaaatttga agagataaac ctcgttcttt cgggaggagc tgcaaagggc | 60 |
| atagcccaca taggtgtttt gaaagctata acgagctcg gtataagggt gagggcttta | 120 |
| agcggggtga gcgccggggc aatcgtttcg gtcttttatg cctcaggcta ctcccctgaa | 180 |
| gggatgttca gccttctgaa gagggtaaac tggctgaagc tgtttaagtt caagccacct | 240 |
| ctgaagggat tgatagggtg ggagaaggct ataagattcc ttgaggaagt tctcccttac | 300 |
| aggagaatag aaaaacttga gataccgacg tatatatgcg cgacggattt atactcggga | 360 |
| agggctctat acctctcgga agggagttta atccccgcac ttctcggcag ctgtgcaatt | 420 |
| cccggcatat ttgaacccgt tgagtataag aattacttgc tcgttgacgg aggtatagtt | 480 |
| aacaaccttc ccgttgagcc ctttcaggaa agcggtattc ccaccgtttg cgttgatgtc | 540 |
| cttcccatag agccggaaaa ggatataaag aacattcttc acatccttt gaggagcttc | 600 |
| tttcttgcgg tccgctcaaa ctccgaaaag agaaggagt tttgtgacct cgttatagtt | 660 |
| cctgagcttg aggagttcac acccttgat gttagaaaag cggaccaaat aatggagagg | 720 |
| ggatacataa aggccttaga ggtactttct gaatag | 756 |

<210> SEQ ID NO 27
<211> LENGTH: 894
<212> TYPE: DNA
<213> ORGANISM: M11TL-29L

<400> SEQUENCE: 27

```
atgtttaata tcaatgtctt tgttaatata tcttggctgt attttttcagg gatagttatg    60 aagactgtgg aagagtatgc gctacttgaa acaggcgtaa gagtgttttta tcggtgtgta   120 atcccggaga agcttttaa cactttgata ataggttcac acggattggg ggcgcacagt    180
ggaatctaca ttagtgttgc tgaagaattt gctaggcacg gatttggatt ctgcatgcac   240
gatcaaaggg gacatgggag aacggcaagc gatagagaaa gagggtatgt ggagggcttt   300
cacaacttca tagaggatat gaaggccttc tccgattatg ccaagtggcg cgtgggaggt   360
gacgaaataa tattgctagg acacagtatg ggcgggctga tagcgctctt aacagttgca   420
acttataaag aaatcgccaa gggagttatc gcgctagccc cggcctcca aatcccctta   480 accccggcta aagacttgt tctaagcctc gcgtcaaggc ttgccccgca ttctaagatc    540
accttacaaa ggagattgcc gcagaaacca gagggttttc aaagagcaaa agatatagaa   600
tacagtctga gtgaaatatc agtcaagctc gtggacgaaa tgattaaagc atcatctatg   660
ttctggacca tagcagggga aattaatact cccgtcctgc ttattcatgg ggaaaaagac   720
aatgtcatac ctccggaggc gagcaaaaaa gcctaccaat taatacttc attccctaaa    780 gagttgaaaa ataccccga tcttggacac aacttgttt ttgaaccagg cgcggtgaaa    840
atcgtcacag acattgtaga gtgggttaag aatctaccca gggaaaatcc ttaa         894

<210> SEQ ID NO 28
<211> LENGTH: 789
<212> TYPE: DNA
<213> ORGANISM: Thermococcus CL-2-30LC

<400> SEQUENCE: 28
atggaggttt acaaggccaa attcggcgaa gcaaagctcg gctgggtcgt tctggttcat    60
ggcctcggcg agcacagcgg aaggtatgga agactgatta aggaactcaa ctatgccggc   120
tttggagttt acaccttcga ctggcccggc acgggaaga gcccgggcaa gagagggcac   180
acgagcgtcg aggaggcgat ggaaatcatc gactcgataa tcgaggagat cagggagaag   240
cccttcctct tcggccacag cctcggtggt ctaactgtca tcaggtacgc tgagacgcgg   300
cccgataaaa tacggggatt aatagcttcc tcgcctgccc tcgccaagag cccggaaacg   360
ccgggcttca tggtggccct cgcgaagttc cttggaaaga tcgcccccgg agttgttctc   420
tccaacggca taaagccgga actcctctcg aggaacaggg acgccgtgag gaggtacgtt   480
gaagacccac tcgtccacga caggatttcg gccaagctgg aaggagcat cttcgtgaac   540 atggagctgg cccacaggga ggcggacaag ataaaagtcc cgatcctcct tctgatcggc   600
actggcgatg taataacccc gcctgaaggc tcacgcagac tcttcgagga gctgccgtc    660 gagaacaaaa ccctgaggga gttcgagggg gcgtaccacg atatttga agacccgag     720 tgggccgagg agttccacga aacaattgtt aagtggctgg ttgaaaaatc gtactcttcg   780
gctcaataa                                                          789

<210> SEQ ID NO 29
<211> LENGTH: 750
<212> TYPE: DNA
<213> ORGANISM: Aquifex VF5-34LC

<400> SEQUENCE: 29
ttgattggca atttgaaatt gaagaggttt gaagaggtta acttagttct ttcgggaggg    60
gctgccaagg gtatcgccca tataggtgtt ttaaaagctc tggaagagct cggtataaag   120
```

```
gtaaagaggc tcagcggggt aagtgctgga gctatcgttt ccgtctttta cgcttcgggc    180
tacactcccg acgagatgtt aaaactcctg aaagaggtaa actggctcaa actttttaag    240
ttcaaaacac cgaaaatggg cttaatgggg tgggagaagg ctgcagagtt tttggaaaaa    300
gagctcggag ttaagaggct ggaagacctg aacataccaa cctatctttg ctcggcggat    360
ctgtacacgg gaaaggctct ttacttcggc agaggtgact taattcccgt gcttctcgga    420
agttgttcca tacccgggat ttttgaacca gttgagtacg agaattttct acttgttgac    480
ggaggtatag tgaacaacct gcccgtagaa cctttggaaa agttcaaaga acccataatc    540
ggggtagatg tgcttcccat aactcaagaa agaaagatta aaatatact ccacatcctt     600 ataaggagct tctttctggc ggttcgttcc aattcggaaa agagaaagga gttctgcaac    660
gtagttatag aacctcccct tgaagagttc tctcctctgg acgtaaataa ggcggacgag    720
atattctgcg gggatatgag agcacttaa                                       750

<210> SEQ ID NO 30
<211> LENGTH: 1017
<212> TYPE: DNA
<213> ORGANISM: Teredinibacter - 42L

<400> SEQUENCE: 30
atgccagcta atgactcacc cacgatcgac tttaatcctc gcggcattct tcgcaacgct     60
cacgcacagg ttattttagc gacttccggc ttgcgcaaag cgttttttgaa acgcacgcac   120 aagagctacc tcagcactgc ccaatggctg gagctcgatg ccggcaacgg agttaccttg    180
gccggagagc ttaacacagc gcctgcaact gcatcctcct cccacccggc gcacaagaac    240
actctggtta ttgtgctgca cggctgggaa ggctccagcc agtcggccta tgcgacctcc    300
gctggcagca cgcttttcga caatgggttc gacactttc gccttaatt  tcgcgatcac    360 ggcgacacct accacttaaa ccgcggcata tttaactcat cgctgattga cgaagtagtg    420
ggcgcagtca aagccatcca gcagcaaacc gactacgaca gtattgcct gatggggttc     480 tcactgggtg ggaactttgc cttgcgcgtc gcggtgcggg aacagcatct cgctaaaccg    540
ctagcgggcg tgctcgccgt atgcccggta ctcgaccccg cacacaccat gatggcccta    600
aaccgaggtg cgttttcta cggccgctat tttgcgcata atggaagcg ctcgttaacc       660 gcaaaacttg cagctttccc agactacaaa tacggcaaag atttaaaatc gatacacacg    720
cttgatgagt taaacaacta tttcattccc cgctacaccg gcttcaactc agtctccgaa    780
tacttcaaaa gttacacgct caccgggcag aagctcgcgt ttctcaactg ccccagttac    840
attctggcag ctggcgacga cccaataatt ccagcatccg acttttcagaa aatagccaag    900 cctgcgaatc tgcacataac agtaacgcaa caaggttctc attgcgcata cctggaaaac    960
ctgcataaac ctagtgctgc cgacaaatat gcggtgaaat tatttggagc ctgttga      1017

<210> SEQ ID NO 31
<211> LENGTH: 936
<212> TYPE: DNA
<213> ORGANISM: Archaeoglobus fulgidus

<400> SEQUENCE: 31
atgcttgata tgccaatcga ccctgtttac taccagcttg ctgagtattt cgacagtctg     60
ccgaagttcg accagttttc ctcggccaga gagtacaggg aggcgataaa tcgaatatac    120
gaggagagaa accggcagct gagccagcat gagagggttg aaagagttga ggacaggacg    180
attaagggga ggaacggaga catcagagtc agagtttacc agcagaagcc cgattccccg    240
```

```
gttctggttt actatcacgg tggtggattt gtgatttgca gcatcgagtc gcacgacgcc    300
ttatgcagga gaattgcgag actttcaaac tctaccgtag tctccgtgga ttacaggctc    360
gctcctgagc acaagtttcc cgccgcagtt tatgattgct acgatgcgac caagtgggtt    420
gctgagaacc gggaggagct gaggattgac ccgtcaaaaa tcttcgttgg ggggacagt     480 gcggagggga tcttgccgc ggcggtttca ataatggcga gagacagcgg agaagatttc     540
ataaagcatc aaattctaat ttaccccgtt gtgaactttg tagcccccac accatcgctt    600
ctggagtttg gagaggggct gtggattctc gaccagaaga taatgagttg gttctcggag    660
cagtacttct ccagagagga agataagttc aaccccctcg cctccgtaat ctttgcggac    720
cttgagaacc tacctcctgc gctgatcata accgccgaat acgacccgct gagagatgaa    780
ggagaagttt tcgggcagat gctgagaaga gccggtgttg aggcgagcat cgtcagatac    840
agaggcgtgc ttcacggatt catcaattac tatcccgtgc tgaaggctgc gagggatgcg    900
ataaaccaga ttgccgctct tcttgtgttc gactag                              936
```

<210> SEQ ID NO 32
<211> LENGTH: 918
<212> TYPE: DNA
<213> ORGANISM: Sulfolobus solfataricus

<400> SEQUENCE: 32

```
atgcccctag atcctagaat taaaaagtta ctagaatcag ctcttactat accaattggt    60
aaagccccag tagaagaggt aagaaagata tttaggcaat tagcgtcggc agctcccaaa   120
gtcgaagttg aaaagtaga agatataaaa ataccaggca gtgaaaccgt tataaacgct   180
agagtgtatt ttccgaagag tagcggtcct tatggtgttc tagtgtatct tcatggaggc   240
ggttttgtaa taggcgatgt ggaatcttat gacccattat gtagagcaat tacaaatgcg   300
tgcaattgcg ttgtagtatc agtggactat aggttagctc cagaatacaa gtttccttct   360
gcagttatcg attcatttga cgctactaat tgggtttata caatttaga taaatttgat    420 ggaaagatgg gagttgcgat tgcgggagat agtgctggag gaaatttggc agcggttgta   480
gctcttcttt caaagggtaa aattaatttg aagtatcaaa tactggttta cccagcggta   540
agtttagata acgtttcaag atccatgata gagtactctg atgggttctt ccttaccaga   600
gagcatatag agtggttcgg ttctcaatac ttacgaagcc ctgcagattt gctagacttt   660
aggttctctc caattctggc gcaagatttc aacggattac ctccagcctt gataataaca   720
gcagaatacg atccactaag ggatcaagga gaagcgtatg caaataaact actacaagct   780
ggagtctcag ttactagtgt gagatttaac aacgttatac acggattcct ctcattcttt    840
ccgttgatgg agcaaggaag agatgctata ggtctgatag ggtctgtgtt aagacgagta   900 tttatgata aaatttaa                                                   918
```

<210> SEQ ID NO 33
<211> LENGTH: 184
<212> TYPE: PRT
<213> ORGANISM: Staphylothermus Marinus

<400> SEQUENCE: 33

Met Ser Leu Asn Lys His Ser Trp Met Asp Met Ile Ile Phe Ile Leu
1               5                   10                  15

Ser Phe Ser Phe Pro Leu Thr Met Ile Ala Leu Ala Ile Ser Met Ser
            20                  25                  30

```
Ser Trp Phe Asn Ile Trp Asn Asn Ala Leu Ser Asp Leu Gly His Ala
        35                  40                  45

Val Lys Ser Ser Val Ala Pro Ile Phe Asn Leu Gly Leu Ala Ile Gly
 50                  55                  60

Gly Ile Leu Ile Val Ile Val Gly Leu Arg Asn Leu Tyr Ser Trp Ser
 65                  70                  75                  80

Arg Val Lys Gly Ser Leu Ile Ile Ser Met Gly Val Phe Leu Asn Leu
                 85                  90                  95

Ile Gly Val Phe Asp Glu Val Tyr Gly Trp Ile His Phe Leu Val Ser
                100                 105                 110

Val Leu Phe Phe Leu Ser Ile Ile Ala Tyr Phe Ile Ala Ile Ser Ile
            115                 120                 125

Leu Asp Lys Ser Trp Ile Ala Val Leu Leu Ile Ile Gly His Ile Ala
        130                 135                 140

Met Trp Tyr Leu His Phe Ala Ser Glu Ile Pro Arg Gly Ala Ala Ile
145                 150                 155                 160

Pro Glu Leu Leu Ala Val Phe Ser Phe Leu Pro Phe Tyr Ile Arg Asp
                165                 170                 175

Tyr Phe Lys Ser Tyr Thr Lys Arg
            180

<210> SEQ ID NO 34
<211> LENGTH: 346
<212> TYPE: PRT
<213> ORGANISM: Pyrodictium

<400> SEQUENCE: 34

Met Lys Leu Leu Glu Pro Thr Asn Thr Ser Tyr Thr Leu Leu Gln Asp
 1               5                  10                  15

Leu Ala Leu His Phe Ala Phe Tyr Trp Phe Leu Ala Val Tyr Thr Trp
                20                  25                  30

Leu Pro Gly Val Leu Val Arg Gly Val Ala Val Asp Thr Gly Val Ala
            35                  40                  45

Arg Val Pro Gly Leu Gly Arg Arg Gly Lys Arg Leu Leu Leu Ala Ala
 50                  55                  60

Val Ala Val Leu Ala Leu Val Val Ser Val Val Pro Ala Tyr Val
 65                  70                  75                  80

Ala Tyr Ser Ser Leu His Pro Glu Ser Cys Arg Pro Val Ala Pro Glu
                 85                 90                  95

Gly Leu Thr Tyr Lys Glu Phe Ser Val Thr Ala Glu Asp Gly Leu Val
                100                 105                 110

Val Arg Gly Trp Val Leu Gly Pro Gly Ala Gly Asn Pro Val Phe
            115                 120                 125

Val Leu Met His Gly Tyr Thr Gly Cys Arg Ser Ala Pro Tyr Met Ala
        130                 135                 140

Val Leu Ala Arg Glu Leu Val Glu Trp Gly Tyr Pro Val Val Val Phe
145                 150                 155                 160

Asp Phe Arg Gly His Gly Glu Ser Gly Ser Thr Thr Ile Gly Pro
                165                 170                 175

Arg Glu Val Leu Asp Ala Arg Ala Val Val Gly Tyr Val Ser Glu Arg
                180                 185                 190

Phe Pro Gly Arg Arg Ile Ile Leu Val Gly Phe Ser Met Gly Gly Ala
            195                 200                 205

Val Ala Ile Val Glu Gly Ala Gly Asp Pro Arg Val Tyr Ala Val Ala
        210                 215                 220
```

```
Ala Asp Ser Pro Tyr Tyr Arg Leu Arg Asp Val Ile Pro Arg Trp Leu
225                 230                 235                 240

Glu Tyr Lys Thr Pro Leu Pro Gly Trp Val Gly Val Leu Ala Gly Phe
                245                 250                 255

Tyr Gly Arg Leu Met Ala Gly Val Asp Leu Gly Phe Gly Pro Ala Gly
            260                 265                 270

Val Glu Arg Val Asp Lys Pro Leu Leu Val Val Tyr Gly Pro Arg Asp
            275                 280                 285

Pro Leu Val Thr Arg Asp Glu Ala Arg Ser Leu Ala Ser Arg Ser Pro
            290                 295                 300

Cys Gly Arg Leu Val Glu Val Pro Gly Ala Gly His Val Glu Ala Val
305                 310                 315                 320

Asp Val Leu Gly Pro Gly Arg Tyr Ala Asp Met Leu Ile Glu Leu Ala
                325                 330                 335

His Glu Glu Cys Pro Pro Gly Ala Gly Gly
                340                 345
```

<210> SEQ ID NO 35
<211> LENGTH: 262
<212> TYPE: PRT
<213> ORGANISM: Archaeoglobus Veneficus

<400> SEQUENCE: 35

```
Met Pro Tyr Val Arg Asn Gly Gly Val Asn Ile Tyr Tyr Glu Leu Val
1               5                   10                  15

Asp Gly Pro Glu Pro Ile Val Phe Val His Gly Trp Thr Ala Asn
                20                  25                  30

Met Asn Phe Trp Lys Glu Gln Arg Arg Tyr Phe Ala Gly Arg Asn Met
            35                  40                  45

Met Leu Phe Val Asp Asn Arg Gly His Gly Arg Ser Asp Lys Pro Leu
50                  55                  60

Gly Tyr Asp Phe Tyr Arg Phe Glu Asn Phe Ile Ser Asp Leu Asp Ala
65                  70                  75                  80

Val Val Arg Glu Thr Gly Val Glu Lys Phe Val Leu Val Gly His Ser
                85                  90                  95

Phe Gly Thr Met Ile Ser Met Lys Tyr Cys Ser Glu Tyr Arg Asn Arg
            100                 105                 110

Val Leu Ala Leu Ile Leu Ile Gly Gly Ser Arg Ile Lys Leu Leu
        115                 120                 125

His Arg Ile Gly Tyr Pro Leu Ala Lys Ile Leu Ala Ser Ile Ala Tyr
    130                 135                 140

Lys Lys Ser Ser Arg Leu Val Ala Asp Leu Ser Phe Gly Lys Asn Ala
145                 150                 155                 160

Gly Glu Leu Lys Glu Trp Gly Trp Lys Gln Ala Met Asp Tyr Thr Pro
                165                 170                 175

Ser Tyr Val Ala Met Tyr Thr Tyr Arg Thr Leu Thr Lys Val Asn Leu
            180                 185                 190

Glu Asn Ile Leu Glu Lys Ile Asp Cys Pro Thr Leu Ile Ile Val Gly
        195                 200                 205

Glu Glu Asp Ala Leu Leu Pro Val Ser Lys Ser Val Glu Leu Ser Arg
    210                 215                 220

Arg Ile Glu Asn Ser Lys Leu Val Ile Pro Asn Ser Gly His Cys
225                 230                 235                 240

Val Met Leu Glu Ser Pro Ser Glu Val Asn Arg Ala Met Asp Glu Phe
```

-continued

```
                245                 250                 255
Ile Ser Ser Ala Gln Phe
            260

<210> SEQ ID NO 36
<211> LENGTH: 251
<212> TYPE: PRT
<213> ORGANISM: Aquifex pyrophilus

<400> SEQUENCE: 36

Leu Arg Leu Arg Lys Phe Glu Glu Ile Asn Leu Val Leu Ser Gly Gly
1               5                   10                  15

Ala Ala Lys Gly Ile Ala His Ile Gly Val Leu Lys Ala Ile Asn Glu
            20                  25                  30

Leu Gly Ile Arg Val Arg Ala Leu Ser Gly Val Ser Ala Gly Ala Ile
        35                  40                  45

Val Ser Val Phe Tyr Ala Ser Gly Tyr Ser Pro Glu Gly Met Phe Ser
    50                  55                  60

Leu Leu Lys Arg Val Asn Trp Leu Lys Leu Phe Lys Phe Lys Pro Pro
65                  70                  75                  80

Leu Lys Gly Leu Ile Gly Trp Glu Lys Ala Ile Arg Phe Leu Glu Glu
                85                  90                  95

Val Leu Pro Tyr Arg Arg Ile Glu Lys Leu Glu Ile Pro Thr Tyr Ile
            100                 105                 110

Cys Ala Thr Asp Leu Tyr Ser Gly Arg Ala Leu Tyr Leu Ser Glu Gly
        115                 120                 125

Ser Leu Ile Pro Ala Leu Leu Gly Ser Cys Ala Ile Pro Gly Ile Phe
    130                 135                 140

Glu Pro Val Glu Tyr Lys Asn Tyr Leu Leu Val Asp Gly Gly Ile Val
145                 150                 155                 160

Asn Asn Leu Pro Val Glu Pro Phe Gln Glu Ser Gly Ile Pro Thr Val
                165                 170                 175

Cys Val Asp Val Leu Pro Ile Glu Pro Glu Lys Asp Ile Lys Asn Ile
            180                 185                 190

Leu His Ile Leu Leu Arg Ser Phe Phe Leu Ala Val Arg Ser Asn Ser
        195                 200                 205

Glu Lys Arg Lys Glu Phe Cys Asp Leu Val Ile Val Pro Glu Leu Glu
    210                 215                 220

Glu Phe Thr Pro Leu Asp Val Arg Lys Ala Asp Gln Ile Met Glu Arg
225                 230                 235                 240

Gly Tyr Ile Lys Ala Leu Glu Val Leu Ser Glu
                245                 250

<210> SEQ ID NO 37
<211> LENGTH: 297
<212> TYPE: PRT
<213> ORGANISM: M11TL-29L

<400> SEQUENCE: 37

Met Phe Asn Ile Asn Val Phe Val Asn Ile Ser Trp Leu Tyr Phe Ser
1               5                   10                  15

Gly Ile Val Met Lys Thr Val Glu Glu Tyr Ala Leu Leu Glu Thr Gly
            20                  25                  30

Val Arg Val Phe Tyr Arg Cys Val Ile Pro Glu Lys Ala Phe Asn Thr
        35                  40                  45

Leu Ile Ile Gly Ser His Gly Leu Gly Ala His Ser Gly Ile Tyr Ile
```

-continued

```
            50                  55                  60
Ser Val Glu Glu Phe Ala Arg His Gly Phe Gly Phe Cys Met His
 65                  70                  75                  80

Asp Gln Arg Gly His Gly Arg Thr Ala Ser Asp Arg Glu Arg Gly Tyr
                 85                  90                  95

Val Glu Gly Phe His Asn Phe Ile Glu Asp Met Lys Ala Phe Ser Asp
            100                 105                 110

Tyr Ala Lys Trp Arg Val Gly Asp Glu Ile Ile Leu Leu Gly His
            115                 120                 125

Ser Met Gly Gly Leu Ile Ala Leu Leu Thr Val Ala Thr Tyr Lys Glu
            130                 135                 140

Ile Ala Lys Gly Val Ile Ala Leu Ala Pro Ala Leu Gln Ile Pro Leu
145                 150                 155                 160

Thr Pro Ala Arg Arg Leu Val Leu Ser Leu Ala Ser Arg Leu Ala Pro
                165                 170                 175

His Ser Lys Ile Thr Leu Gln Arg Arg Leu Pro Gln Lys Pro Glu Gly
            180                 185                 190

Phe Gln Arg Ala Lys Asp Ile Glu Tyr Ser Leu Ser Glu Ile Ser Val
            195                 200                 205

Lys Leu Val Asp Glu Met Ile Lys Ala Ser Ser Met Phe Trp Thr Ile
210                 215                 220

Ala Gly Glu Ile Asn Thr Pro Val Leu Leu Ile His Gly Glu Lys Asp
225                 230                 235                 240

Asn Val Ile Pro Pro Glu Ala Ser Lys Lys Ala Tyr Gln Leu Ile Pro
                245                 250                 255

Ser Phe Pro Lys Glu Leu Lys Ile Tyr Pro Asp Leu Gly His Asn Leu
            260                 265                 270

Phe Phe Glu Pro Gly Ala Val Lys Ile Val Thr Asp Ile Val Glu Trp
            275                 280                 285

Val Lys Asn Leu Pro Arg Glu Asn Pro
        290                 295

<210> SEQ ID NO 38
<211> LENGTH: 262
<212> TYPE: PRT
<213> ORGANISM: Thermococus CL-2-30LC

<400> SEQUENCE: 38

Met Glu Val Tyr Lys Ala Lys Phe Gly Glu Ala Lys Leu Gly Trp Val
  1               5                  10                  15

Val Leu Val His Gly Leu Gly Glu His Ser Gly Arg Tyr Gly Arg Leu
                 20                  25                  30

Ile Lys Glu Leu Asn Tyr Ala Gly Phe Gly Val Tyr Thr Phe Asp Trp
             35                  40                  45

Pro Gly His Gly Lys Ser Pro Gly Lys Arg Gly His Thr Ser Val Glu
         50                  55                  60

Glu Ala Met Glu Ile Ile Asp Ser Ile Ile Glu Glu Ile Arg Glu Lys
 65                  70                  75                  80

Pro Phe Leu Phe Gly His Ser Leu Gly Gly Leu Thr Val Ile Arg Tyr
                 85                  90                  95

Ala Glu Thr Arg Pro Asp Lys Ile Arg Gly Leu Ile Ala Ser Ser Pro
            100                 105                 110

Ala Leu Ala Lys Ser Pro Glu Thr Pro Gly Phe Met Val Ala Leu Ala
            115                 120                 125
```

```
Lys Phe Leu Gly Lys Ile Ala Pro Gly Val Val Leu Ser Asn Gly Ile
        130                 135                 140

Lys Pro Glu Leu Leu Ser Arg Asn Arg Asp Ala Val Arg Arg Tyr Val
145                 150                 155                 160

Glu Asp Pro Leu Val His Asp Arg Ile Ser Ala Lys Leu Gly Arg Ser
                165                 170                 175

Ile Phe Val Asn Met Glu Leu Ala His Arg Glu Ala Asp Lys Ile Lys
            180                 185                 190

Val Pro Ile Leu Leu Ile Gly Thr Gly Asp Val Ile Thr Pro Pro
        195                 200                 205

Glu Gly Ser Arg Arg Leu Phe Glu Glu Leu Ala Val Glu Asn Lys Thr
        210                 215                 220

Leu Arg Glu Phe Glu Gly Ala Tyr His Glu Ile Phe Glu Asp Pro Glu
225                 230                 235                 240

Trp Ala Glu Glu Phe His Glu Thr Ile Val Lys Trp Leu Val Glu Lys
                245                 250                 255

Ser Tyr Ser Ser Ala Gln
            260

<210> SEQ ID NO 39
<211> LENGTH: 249
<212> TYPE: PRT
<213> ORGANISM: Aquifex VF5-34LC

<400> SEQUENCE: 39

Leu Ile Gly Asn Leu Lys Leu Lys Arg Phe Glu Glu Val Asn Leu Val
1               5                   10                  15

Leu Ser Gly Gly Ala Ala Lys Gly Ile Ala His Ile Gly Val Leu Lys
            20                  25                  30

Ala Leu Glu Glu Leu Gly Ile Lys Val Lys Arg Leu Ser Gly Val Ser
        35                  40                  45

Ala Gly Ala Ile Val Ser Val Phe Tyr Ala Ser Gly Tyr Thr Pro Asp
    50                  55                  60

Glu Met Leu Lys Leu Leu Lys Glu Val Asn Trp Leu Lys Leu Phe Lys
65                  70                  75                  80

Phe Lys Thr Pro Lys Met Gly Leu Met Gly Trp Glu Lys Ala Ala Glu
                85                  90                  95

Phe Leu Glu Lys Glu Leu Gly Val Lys Arg Leu Glu Asp Leu Asn Ile
            100                 105                 110

Pro Thr Tyr Leu Cys Ser Ala Asp Leu Tyr Thr Gly Lys Ala Leu Tyr
        115                 120                 125

Phe Gly Arg Gly Asp Leu Ile Pro Val Leu Leu Gly Ser Cys Ser Ile
    130                 135                 140

Pro Gly Ile Phe Glu Pro Val Glu Tyr Glu Asn Phe Leu Leu Val Asp
145                 150                 155                 160

Gly Gly Ile Val Asn Asn Leu Pro Val Glu Pro Leu Glu Lys Phe Lys
                165                 170                 175

Glu Pro Ile Ile Gly Val Asp Val Leu Pro Ile Thr Gln Glu Arg Lys
            180                 185                 190

Ile Lys Asn Ile Leu His Ile Leu Ile Arg Ser Phe Phe Leu Ala Val
        195                 200                 205

Arg Ser Asn Ser Glu Lys Arg Lys Glu Phe Cys Asn Val Val Ile Glu
    210                 215                 220

Pro Pro Leu Glu Glu Phe Ser Pro Leu Asp Val Asn Lys Ala Asp Glu
225                 230                 235                 240
```

```
Ile Phe Cys Gly Asp Met Arg Ala Leu
                245

<210> SEQ ID NO 40
<211> LENGTH: 338
<212> TYPE: PRT
<213> ORGANISM: Teredinibacter - 42

<400> SEQUENCE: 40

Met Pro Ala Asn Asp Ser Pro Thr Ile Asp Phe Asn Pro Arg Gly Ile
1               5                   10                  15

Leu Arg Asn Ala His Ala Gln Val Ile Leu Ala Thr Ser Gly Leu Arg
            20                  25                  30

Lys Ala Phe Leu Lys Arg Thr His Lys Ser Tyr Leu Ser Thr Ala Gln
        35                  40                  45

Trp Leu Glu Leu Asp Ala Gly Asn Gly Val Thr Leu Ala Gly Glu Leu
    50                  55                  60

Asn Thr Ala Pro Ala Thr Ala Ser Ser His Pro Ala His Lys Asn
65                  70                  75                  80

Thr Leu Val Ile Val Leu His Gly Trp Glu Gly Ser Ser Gln Ser Ala
                85                  90                  95

Tyr Ala Thr Ser Ala Gly Ser Thr Leu Phe Asp Asn Gly Phe Asp Thr
            100                 105                 110

Phe Arg Leu Asn Phe Arg Asp His Gly Asp Thr Tyr His Leu Asn Arg
        115                 120                 125

Gly Ile Phe Asn Ser Ser Leu Ile Asp Glu Val Val Gly Ala Val Lys
    130                 135                 140

Ala Ile Gln Gln Gln Thr Asp Tyr Asp Lys Tyr Cys Leu Met Gly Phe
145                 150                 155                 160

Ser Leu Gly Gly Asn Phe Ala Leu Arg Val Ala Val Arg Glu Gln His
                165                 170                 175

Leu Ala Lys Pro Leu Ala Gly Val Leu Ala Val Cys Pro Val Leu Asp
            180                 185                 190

Pro Ala His Thr Met Met Ala Leu Asn Arg Gly Ala Phe Phe Tyr Gly
        195                 200                 205

Arg Tyr Phe Ala His Lys Trp Lys Arg Ser Leu Thr Ala Lys Leu Ala
    210                 215                 220

Ala Phe Pro Asp Tyr Lys Tyr Gly Lys Asp Leu Lys Ser Ile His Thr
225                 230                 235                 240

Leu Asp Glu Leu Asn Asn Tyr Phe Ile Pro Arg Tyr Thr Gly Phe Asn
                245                 250                 255

Ser Val Ser Glu Tyr Phe Lys Ser Tyr Thr Leu Thr Gly Gln Lys Leu
            260                 265                 270

Ala Phe Leu Asn Cys Pro Ser Tyr Ile Leu Ala Ala Gly Asp Asp Pro
        275                 280                 285

Ile Ile Pro Ala Ser Asp Phe Gln Lys Ile Ala Lys Pro Ala Asn Leu
    290                 295                 300

His Ile Thr Val Thr Gln Gln Gly Ser His Cys Ala Tyr Leu Glu Asn
305                 310                 315                 320

Leu His Lys Pro Ser Ala Ala Asp Lys Tyr Ala Val Lys Leu Phe Gly
                325                 330                 335

Ala Cys

<210> SEQ ID NO 41
```

<211> LENGTH: 311
<212> TYPE: PRT
<213> ORGANISM: Archaeoglobus fulgidus

<400> SEQUENCE: 41

```
Met Leu Asp Met Pro Ile Asp Pro Val Tyr Tyr Gln Leu Ala Glu Tyr
1               5                   10                  15

Phe Asp Ser Leu Pro Lys Phe Asp Gln Phe Ser Ser Ala Arg Glu Tyr
            20                  25                  30

Arg Glu Ala Ile Asn Arg Ile Tyr Glu Glu Arg Asn Arg Gln Leu Ser
        35                  40                  45

Gln His Glu Arg Val Glu Arg Val Glu Asp Arg Thr Ile Lys Gly Arg
    50                  55                  60

Asn Gly Asp Ile Arg Val Arg Val Tyr Gln Gln Lys Pro Asp Ser Pro
65                  70                  75                  80

Val Leu Val Tyr Tyr His Gly Gly Phe Val Ile Cys Ser Ile Glu
                85                  90                  95

Ser His Asp Ala Leu Cys Arg Arg Ile Ala Arg Leu Ser Asn Ser Thr
                100                 105                 110

Val Val Ser Val Asp Tyr Arg Leu Ala Pro Glu His Lys Phe Pro Ala
            115                 120                 125

Ala Val Tyr Asp Cys Tyr Asp Ala Thr Lys Trp Val Ala Glu Asn Ala
        130                 135                 140

Glu Leu Arg Ile Asp Pro Ser Lys Ile Phe Val Gly Gly Asp Ser
145                 150                 155                 160

Ala Gly Gly Asn Leu Ala Ala Val Ser Ile Met Ala Arg Asp Ser
                165                 170                 175

Gly Glu Asp Phe Ile Lys His Gln Ile Leu Ile Tyr Pro Val Val Asn
            180                 185                 190

Phe Val Ala Pro Thr Pro Ser Leu Leu Glu Phe Gly Glu Gly Leu Trp
        195                 200                 205

Ile Leu Asp Gln Lys Ile Met Ser Trp Phe Ser Glu Gln Tyr Phe Ser
    210                 215                 220

Arg Glu Glu Asp Lys Phe Asn Pro Leu Ala Ser Val Ile Phe Ala Asp
225                 230                 235                 240

Leu Glu Asn Leu Pro Pro Ala Leu Ile Ile Thr Ala Glu Tyr Asp Pro
                245                 250                 255

Leu Arg Asp Glu Gly Glu Val Phe Gly Gln Met Leu Arg Arg Ala Gly
            260                 265                 270

Val Glu Ala Ser Ile Val Arg Tyr Arg Gly Val Leu His Gly Phe Ile
        275                 280                 285

Asn Tyr Tyr Pro Val Leu Lys Ala Ala Arg Asp Ala Ile Asn Gln Ile
    290                 295                 300

Ala Ala Leu Leu Val Phe Asp
305                 310
```

<210> SEQ ID NO 42
<211> LENGTH: 305
<212> TYPE: PRT
<213> ORGANISM: Sulfolobus solfataricus

<400> SEQUENCE: 42

```
Met Pro Leu Asp Pro Arg Ile Lys Lys Leu Leu Glu Ser Ala Leu Thr
1               5                   10                  15

Ile Pro Ile Gly Lys Ala Pro Val Glu Glu Val Arg Lys Ile Phe Arg
            20                  25                  30
```

```
Gln Leu Ala Ser Ala Ala Pro Lys Val Glu Val Gly Lys Val Glu Asp
             35                  40                  45

Ile Lys Ile Pro Gly Ser Glu Thr Val Ile Asn Ala Arg Val Tyr Phe
         50                  55                  60

Pro Lys Ser Ser Gly Pro Tyr Gly Val Leu Val Tyr Leu His Gly Gly
 65              70                  75                      80

Gly Phe Val Ile Gly Asp Val Glu Ser Tyr Asp Pro Leu Cys Arg Ala
                 85                  90                  95

Ile Thr Asn Ala Cys Asn Cys Val Val Val Ser Val Asp Tyr Arg Leu
            100                 105                 110

Ala Pro Glu Tyr Lys Phe Pro Ser Ala Val Ile Asp Ser Phe Asp Ala
            115                 120                 125

Thr Asn Trp Val Tyr Asn Asn Leu Asp Lys Phe Asp Gly Lys Met Gly
            130                 135                 140

Val Ala Ile Ala Gly Asp Ser Ala Gly Gly Asn Leu Ala Ala Val Val
145                 150                 155                 160

Ala Leu Leu Ser Lys Gly Lys Ile Asn Leu Lys Tyr Gln Ile Leu Val
                165                 170                 175

Tyr Pro Ala Val Ser Leu Asp Asn Val Ser Arg Ser Met Ile Glu Tyr
                180                 185                 190

Ser Asp Gly Phe Phe Leu Thr Arg Glu His Ile Glu Trp Phe Gly Ser
            195                 200                 205

Gln Tyr Leu Arg Ser Pro Ala Asp Leu Leu Asp Phe Arg Phe Ser Pro
            210                 215                 220

Ile Leu Ala Gln Asp Phe Asn Gly Leu Pro Pro Ala Leu Ile Ile Thr
225                 230                 235                 240

Ala Glu Tyr Asp Pro Leu Arg Asp Gln Gly Glu Ala Tyr Ala Asn Lys
                245                 250                 255

Leu Leu Gln Ala Gly Val Ser Val Thr Ser Val Arg Phe Asn Asn Val
            260                 265                 270

Ile His Gly Phe Leu Ser Phe Phe Pro Leu Met Glu Gln Gly Arg Asp
            275                 280                 285

Ala Ile Gly Leu Ile Gly Ser Val Leu Arg Arg Val Phe Tyr Asp Lys
            290                 295                 300

Ile
305
```